United States Patent [19]

Shiba

[11] Patent Number: 5,243,987
[45] Date of Patent: Sep. 14, 1993

[54] APPARATUS FOR OBTAINING BLOOD BACKSCATTERING POWER EXCLUDING CLUTTER COMPONENTS

[75] Inventor: Akira Shiba, Kawasaki, Japan
[73] Assignee: Fujitsu Limited, Kawasaki, Japan
[21] Appl. No.: 766,090
[22] Filed: Sep. 27, 1991

[30] Foreign Application Priority Data

Sep. 28, 1990 [JP] Japan .................. 2-259398

[51] Int. Cl.⁵ .............................. A61B 8/00
[52] U.S. Cl. ...................... 128/660.06; 128/661.07
[58] Field of Search ............... 128/660.01, 660.06, 128/660.07, 661.08–661.1

[56] References Cited

U.S. PATENT DOCUMENTS

| | | | |
|---|---|---|---|
| 4,152,928 | 5/1979 | Roberts | 73/61 R |
| 4,867,167 | 9/1989 | Magnin | 128/660.06 |
| 4,873,984 | 10/1989 | Hunt et al. | 128/660.07 |
| 4,881,549 | 11/1989 | Rhyne | 128/660.07 |
| 4,993,418 | 2/1991 | Weaver et al. | 128/661.08 |
| 5,095,909 | 3/1992 | Nakayama et al. | 128/660.06 |

FOREIGN PATENT DOCUMENTS

| | | |
|---|---|---|
| 0050040 | 4/1982 | European Pat. Off. |
| 2371182 | 6/1978 | France |
| 2377628 | 8/1978 | France |
| 1-297052 | 12/1989 | Japan |

OTHER PUBLICATIONS

Yamada, I. et al "UTS Diagnostic Equipment for Deep Organs such as Heart" EP 0383288 published 22 Aug. 1990.
Brandestini, M. A. et al "Blood Flow Imaging Using a Discrete Time-Frequency Meter" 1978 UTS Symp. Proc. IEEE Cat. #78 CH 1344-1SU Cherry Hill, N.J. 25-27 Sep. 1978 pp. 348-352.
K. Nakayama and S. Yagi, "In Vivo Tissue Characterization Using Blood Flow Doppler Signal as a Reference," Japanese Journal of Medical Ultrasonics, vol. 15, Supplement I, 1988 (Jun. 4, 1988, in Japanese).
S. Miyagi et al., The Technical Report of the Institute of Electronics, Information and Communication Engineers, vol. 88, No. 307, US-88-47 (Dec. 1, 1988, in Japanese).
The Journal of Acoustic Society of America, vol. 83, No. 4, 1 Apr. 1988, New York, pp. 1639–1644; Roos et al.: "Application of 30-mhz acoustic scattering to the study of human red blood cells".
Medical and Biological Engineering, vol. 11, No. 6, 1 Nov. 1973, pp. 766–770; Baker et al.: "Technique for studying the sample volume of ultrasonic Doppler devices".
Journal of the Acoustic Society of America, vol. 75, No. 4, 1 Apr. 1984, New York, pp. 1265–1272; Shung et al.: "Effect of flow disturbance on ultrasonic backscatter from blood".

Primary Examiner—Francis Jaworski
Attorney, Agent, or Firm—Staas & Halsey

[57] ABSTRACT

An apparatus for obtaining a blood backscattering power, comprising a signal input unit for inputting an electric signal which is converted from an ultrasound signal which has been generated in a certain depth in the human body by reflecting or backscattering; a Doppler spectrum obtaining unit for obtaining a Doppler spectrum which contains information on a distribution of an intensity of the above electric signal as a function of a time and a Doppler frequency, where the Doppler frequency is a quantity indicating a velocity component in a direction of the above transmitted ultrasound signal, of an object which backscatters the transmitted ultrasound signal; a Doppler frequency range determining unit for determining an elimination frequency range of the above Doppler frequency for each time; and an accumulating unit for accumulating the above intensity over a whole range of the above Doppler frequency except the above elimination frequency range for each time, to obtain a blood backscattering power of the time. The apparatus may further contain: a time range determining unit for determining an efective time range; and an averaging unit for averaging the above blood backscattering power over the efective time range to obtain an average of the above blood backscattering power in the efective time range.

18 Claims, 16 Drawing Sheets

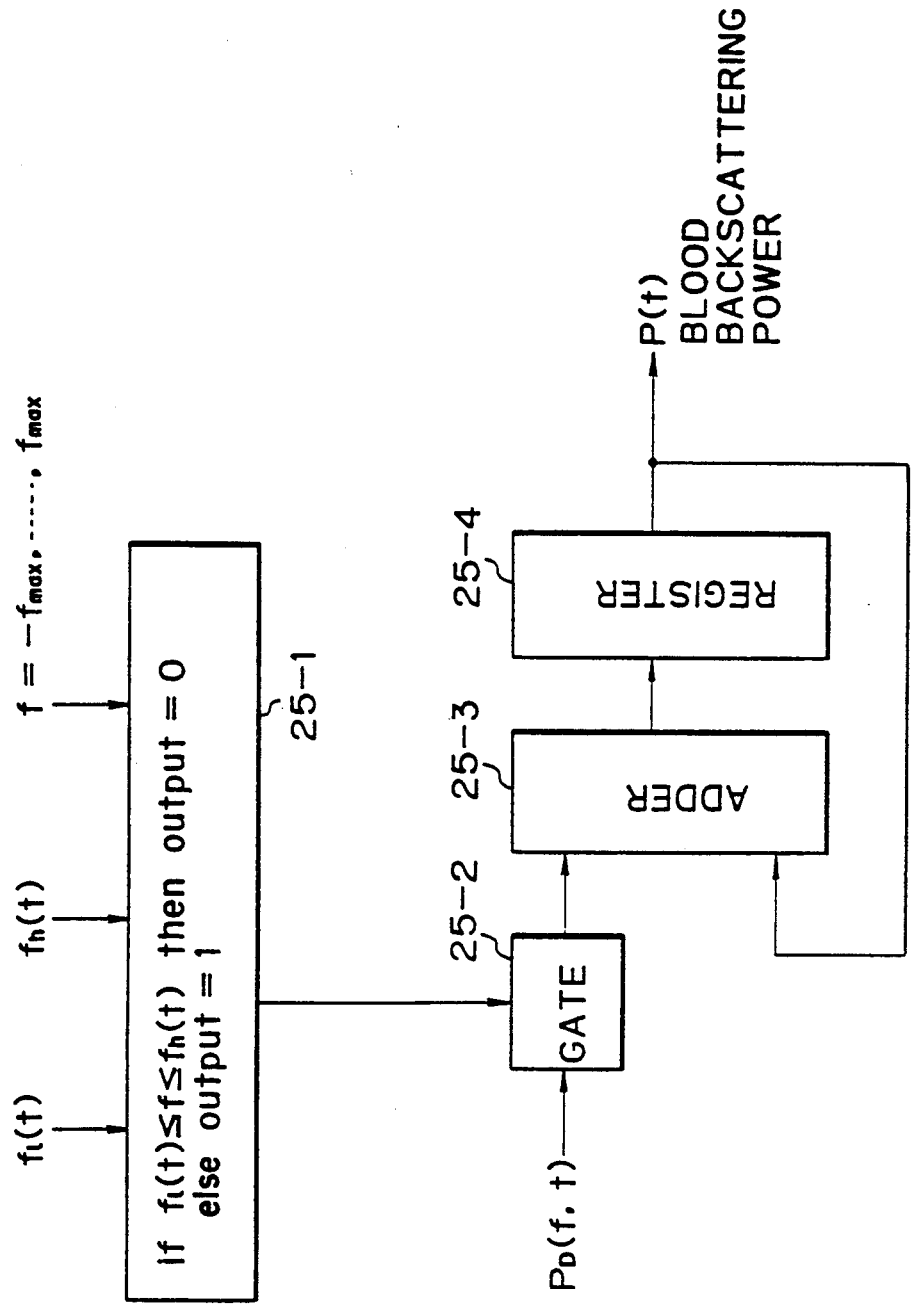

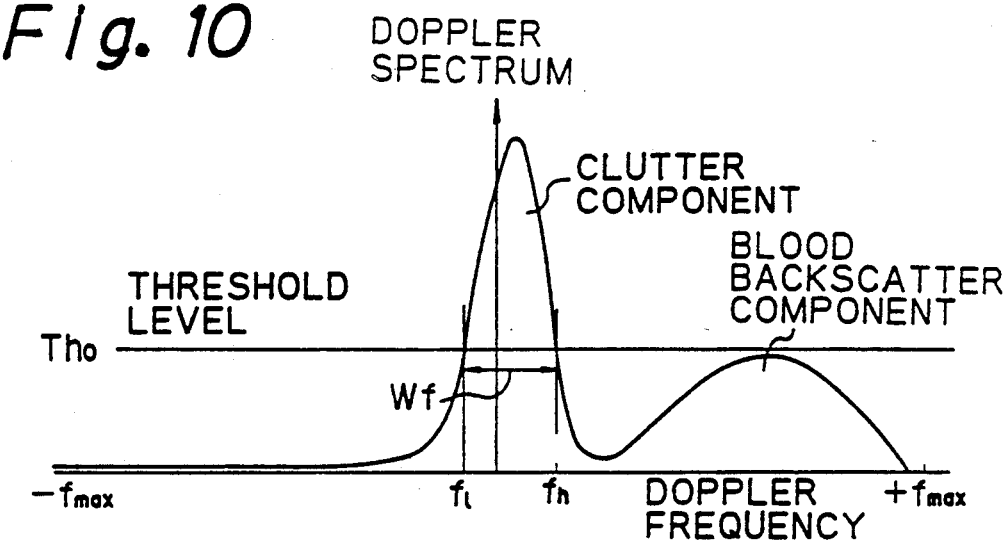
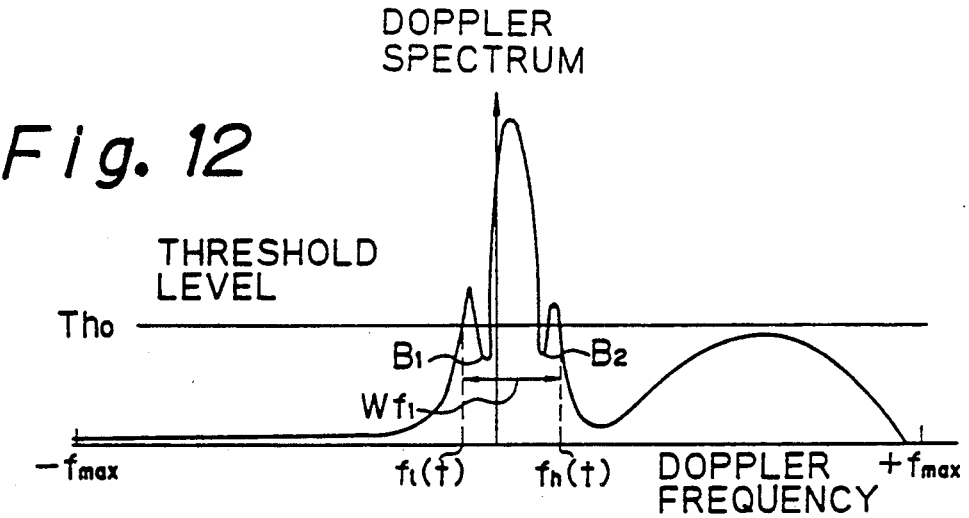
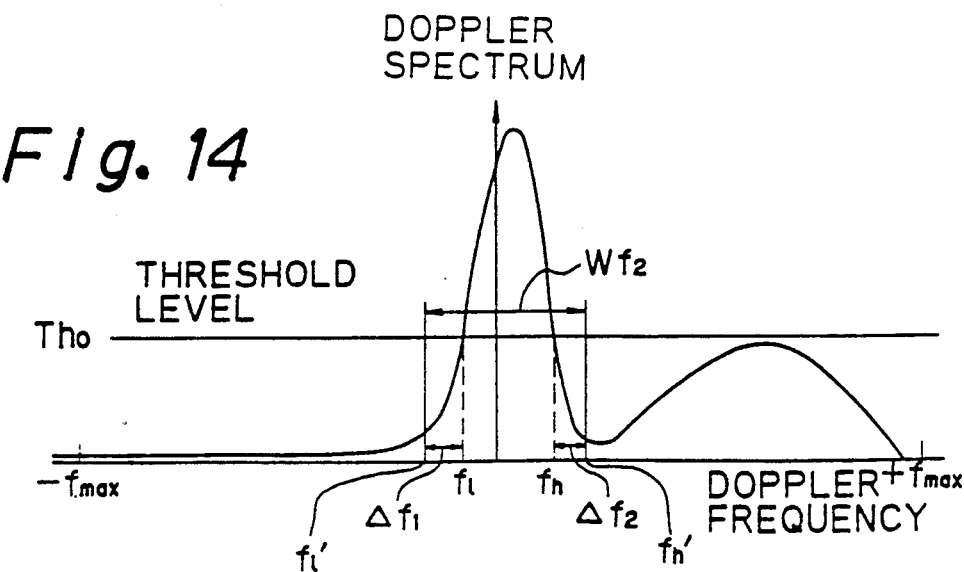

APPARATUS FOR OBTAINING BLOOD BACKSCATTERING POWER EXCLUDING CLUTTER COMPONENTS

CROSS-REFERENCE TO RELATED APPLICATION

This application is related to application Ser. No. 07/356,888 filed May 25, 1989, having the same inventor and the same assignee as the subject application.

BACKGROUND OF THE INVENTION (1) Field of the Invention

The present invention relates to a blood backscattering power obtaining apparatus used in ultrasonography. Recently, in the field of ultrasonography, the blood backscattering power has been used as a reference value for evaluating the intensity of a backscattering power of a tissue.

(2) Description of the Related Art

It is known that the backscattering power of a portion of a tissue in a human body provides useful information on a morbid state of the portion of the tissue. For, example, a tissue of a heart suffering from myocardial or cardiac infarction gives a higher value of the backscattering power compared with a normal tissue of a heart, and a fatty liver also gives a higher value of the backscattering power compared with a normal tissue of a liver.

Intensities of an ultrasound signal propagated from an ultrasonic transducer to an objective portion of a tissue, and an ultrasound signal generated by blood backscattering, propagated to the ultrasonic transducer, are attenuated with their propagation lengths, and the degree of the attenuation depends on the characterization of the tissues through which the ultrasound signals propagate.

Since it is known that the backscattering power of blood does not essentially vary between different persons, and a large blood vessel or a portion containing blood usually exists near a tissue of which the blood backscattering power is to be measured, it is proposed to use the backscattering power of blood in a large blood vessel or a body containing blood, e.g., the heart or other organ, near a tissue of which a blood backscattering power is to be measured, as a reference value for evaluating the degree of the attenuation which an ultrasound signal is suffered while the ultrasound signal is propagated from an ultrasonic transducer to the tissue, is backscattered by the tissue, and is propagate back to the ultrasonic transducer i.e., evaluating the backscattering power of the tissue. This technique is proposed by K. Nakayama and S. Yagi in "In Vivo Tissue Characterization Using Blood Flow Doppler Signal as a Reference" in Japanese Journal of Medical Ultrasonics, Vol. 15, Supplement I, 1988 (Jun. 4, 1988, in Japanese), by S. Miyagi et al. in the Technical Report of the Institute of Electronics, Information and Communication Engineers, Vol. 88, No. 307, US-88-47 (Dec. 1, 1988, in Japanese), by the Unexamined Japanese Patent Publication No. 1-297052 (Dec. 30, 1989), and by the U.S. Pat. No. 4,867,167 granted to P. A. Magnin on Sep. 19, 1989. Although the blood backscattering power varies with a hematocrit value of blood (a volume ratio of blood cells in blood), the hematocrit value can be measured, and therefore, a blood backscattering power of an individual person can be corrected by his hematocrit value.

The outline of the above technique is schematically indicated in FIG. 1. In FIG. 1, reference numeral 1 denotes an ultrasonic transducer, 2 denotes an ultrasonic beam, 4 denotes a vessel which is filled with blood, 5 denotes a portion of the tissue which is to be examined, and 6 denotes the position in the blood vessel at which a value of the blood backscattering power is obtained. The above position in the vessel which is filled with blood, may be the interior a blood vessel, or a ventricle or an atrium cordis of a heart.

However, it is known that ultrasound signals which are generated by the blood backscattering are detected by the ultrasonic transducer together with strong clutter components. FIG. 2 shows several examples of causes of the clutter components. In FIG. 2, reference numeral 1 denotes the a ultrasonic transducer, 11 denotes wall of a blood vessel, 12 denotes inside of the blood vessel, 13 denotes a main beam of an ultrasound signal, 14 denotes a position at which the blood backscattering power is to be obtained, 15, 17, 19, and 21 each denote a side lobe beam of the main beam of the ultrasound signal, 16 and 18 each denote a portion of the wall of the blood vessel located at a position of the same propagation delay D, i.e., distance from the ultrasonic transducer as the position 14 of the blood backscattering, and 20 and 22 each denote a portion of a tissue not of interest, but which is located at a position of the same propagation delay D from the ultrasonic transducer as the position 14 of the blood backscattering. As understood from FIG. 2, ultrasound signals which have been reflected at boundaries of different tissues 16, 18, or backscattered in some tissues 20 and 22 which are not of interest, reach the ultrasonic transducer 1 at the same time as ultrasound signals which have been generated by the blood backscattering in the vessel to be examined. Namely, the ultrasound signals which have been reflected at boundaries of different tissues or backscattered in some tissues which are not of interest, are superimposed on the ultrasound signals which have been generated by the blood backscattering. It is known that the intensities of the ultrasound signals which are generated by the blood backscattering are smaller than the intensities of the clutter components, the ultrasound signals which have been reflected at boundaries of different tissues or backscattered in some tissues which are not of interest, by about 30 to 50 dB.

Therefore, it is necessary to effectively remove the clutter components, when obtaining the blood backscattering power, from the above ultrasound signals which include the blood backscattering component and the clutter components.

SUMMARY OF THE INVENTION

An object of the present invention is to provide an apparatus for obtaining a blood backscatter power wherein clutter components, superimposed on the desired ultrasound signals which are generated by blood backscattering, can be effectively removed.

According to the first aspect of the present invention, there is provided an apparatus for obtaining the blood backscattering power, while comprises an ultrasound signal transmitting unit for transmitting an ultrasound signal into a human body, a signal converting unit for receiving an ultrasound signal which is generated in various portions in the human body by reflecting or backscattering the above transmitted ultrasound signal, and converting the received ultrasound signal to an electric signal, a signal input unit for inputting the electric signal which is converted from the received ultrasound signal which has been generated in a certain depth in the human body by reflecting or backscattering the above transmitted ultrasound signal, a Doppler spectrum obtaining unit for obtaining a Doppler spectrum which contains information on a distribution of an intensity of the above electric signal as a function of a time course and a Doppler frequency, where the Doppler frequency is a quantity indicating a velocity component in a direction of the above transmitted ultrasound signal, of an object i.e., the above portions of the human body, which backscatters the transmitted ultrasound signal, a Doppler frequency range determining unit for determining an elimination frequency range of the above Doppler frequency for each of a plurality of determination times and an accumulating unit for above intensity over a whole range of the above Doppler frequency except the above elimination frequency range each determination time, to obtain a blood backscattering power an a function of time.

According to the second aspect of the present invention, in addition to the construction of the first aspect of the present invention, the above Doppler frequency range determining unit may comprise an input unit for manually inputting the above elimination frequency range for each determination time.

According to the third aspect of the present invention, in addition to the construction of the second aspect of the present invention, the above Doppler frequency range determining unit may comprise a memory unit for memorizing the above elimination frequency range for each determination time.

According to the fourth aspect of the present invention, in addition to the construction of the second aspect of the present invention, the above Doppler frequency range determining unit may comprise a display unit for displaying the above Doppler spectrum, and the above elimination frequency range.

According to the fifth aspect of the present invention, in addition to the construction of the first aspect of the present invention, the above Doppler frequency range determining unit may comprise a comparator unit for comparing the above intensity with a threshold level.

According to the sixth aspect of the present invention, in addition to the construction of the fifth aspect of the present invention, the above accumulating unit may comprise a gate unit for receiving the output of the above comparator unit and not allowing a supply of the above intensity to pass the accumulating unit when the above intensity is larger than the above threshold level.

According to the seventh aspect of the present invention, in addition to the construction of the fifth aspect of the present invention, the above Doppler frequency range determining unit may comprise a boundaries determining unit for determining a beginning point of the above elimination frequency range as a Doppler frequency at which the above intensity first becomes larger than the above threshold level when scanning a whole range of the Doppler frequency for each time, and determining an end point of the above elimination frequency range as a Doppler frequency at which the above intensity last becomes smaller than the above threshold level when scanning whole range of the Doppler frequency for each determination time.

According to the eighth aspect of the present invention, in addition to the construction of the seventh aspect of the present invention, the above accumulating unit may comprise a gate unit for receiving the above beginning point and the above end point to begin stopping a supply of the above intensity to the accumulating unit at the above beginning point, and start the supply of the above intensity to the accumulating unit at the above end point.

According to the ninth aspect of the present invention, in addition to the construction of the eighth aspect of the present invention, the above Doppler frequency range determining unit may further comprise a boundaries shifting unit for shifting the above beginning point of the above elimination frequency range by a predetermined amount, and shifting the above end point of the above elimination frequency range by a predetermined amount so that the above elimination frequency range is widened to exclude the electric signal in the Doppler frequencies in the vicinity of the above pre-widened elimination frequency range, on both sides thereof, from the accumulating operation in the above accumulating unit.

According to the tenth aspect of the present invention, in addition to the construction of the fifth aspect of the present invention, the above Doppler frequency range determining unit may further comprise an elimination range modifying unit for widening the above elimination frequency range so that the electric signal in the Doppler frequencies in the vicinity of the above pre-widened elimination frequency range, on both sides thereof, is excluded from the operation in the above accumulating unit.

According to the eleventh aspect of the present invention, in addition to the construction of the first aspect of the present invention, the apparatus further contains, a time range determining unit for determining an effective time range of the time; and an averaging unit for averaging the above blood backscattering power over the above effective time range to obtain an average of the above blood backscattering power in the above effective time range.

According to the twelfth aspect of the present invention, in addition to the construction of the eleventh aspect of the present invention, the above time range determining unit comprises an input unit for manually inputting the above effective time range.

According to the thirteenth aspect of the present invention, in addition to the construction of the twelfth aspect of the present invention, the above time range determining unit comprises a memory unit for memorizing the above effective time range.

According to the fourteenth aspect of the present invention, in addition to the construction of the twelfth aspect of the present invention, the above time range determining unit comprises a display unit for displaying the above Doppler spectrum, and the above effective time range.

According t the fifteenth aspect of the present invention, in addition to the construction of the eleventh aspect of the present invention, the above time range determining unit comprises: a dispersion obtaining unit for obtaining a dispersion of the above blood backscattering power, as a function of the above time; and a comparator unit for comparing the above dispersion with a threshold level.

According to the sixteenth aspect of the present invention, in addition to the construction of the fifteenth aspect of the present invention, the above averaging unit comprises a gate unit for receiving the output of the above comparator unit and not allowing a supply of the above blood backscattering power to pass to the averaging unit when the above dispersion is larger than the above threshold level.

According to the seventeenth aspect of the present invention, in addition to the construction of the fifteenth aspect of the present invention, the above time range determining unit comprises a boundaries determining unit for determining a beginning point of the above effective time range as a time at which the above dispersion becomes smaller than the above threshold level, and determining an end point of the above effective time range as a time at which the above dispersion becomes larger than the above threshold level.

According to the eighteenth aspect of the present invention, in addition to the construction of the seventeenth aspect of the present invention, the above averaging unit comprises a gate unit for receiving the above beginning point and the above end point to begin to stop a supply of the above blood backscattering power to the averaging unit at the above end point, and start the supply of the above blood backscattering power to the averaging unit at the above beginning point.

BRIEF DESCRIPTION OF THE DRAWINGS

In the drawings:

FIG. 8 is a diagram showing an example of a construction of the accumulating unit 25 in the construction of FIG. 6;

FIG. 10 is a diagram showing a Doppler spectrum at a certain time for explaining the operation of the construction of FIG. 9;

FIG. 12 is a diagram showing a Doppler spectrum at a certain time for explaining the operation of the construction of FIG. 11;

FIG. 14 is a diagram showing a Doppler spectrum at a certain time for explaining the operation of the construction of FIG. 13;

DESCRIPTION OF THE PREFERRED EMBODIMENTS

Trial Construction for Obtaining Blood Backscattering Power (FIGS. 3, 4, 5A, and 5B)

Figure 3:
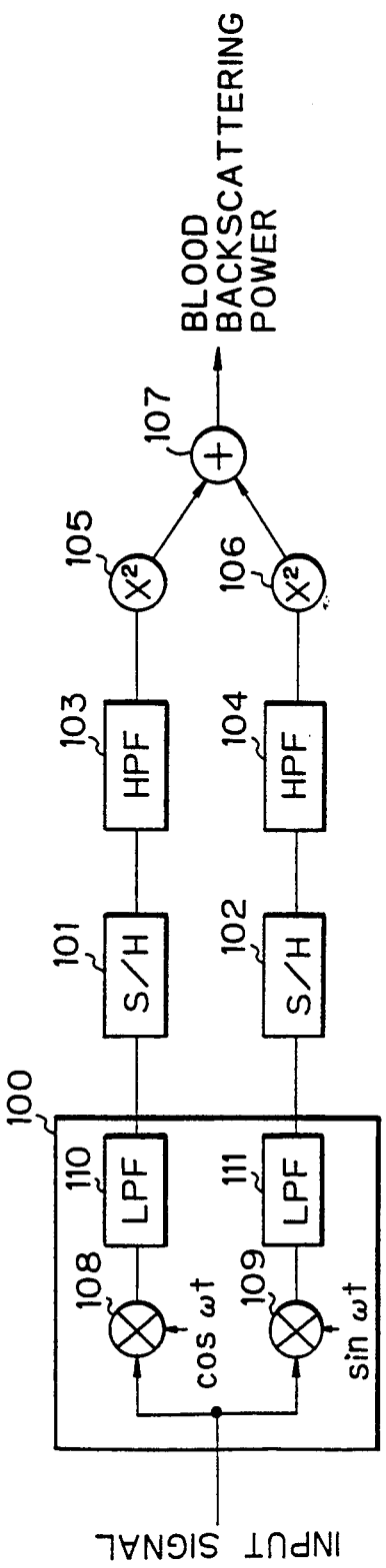
FIG. 3 is a diagram showing a trial construction for obtaining a blood backscattering power.

FIG. 3 is a diagram showing a trail construction for obtaining a blood backscattering power. In FIG. 3, reference numeral 100 denotes a quadrature detector (demodulator) unit, 101 and 102 each denote a sample & hold circuit, 103 and 104 each denote a high-pass filter, 105 and 106 each denote a square calculating unit, and 107 denotes an adder. In the quadrature detector unit 100, reference numeral 108 and 109 each denote a multiplier, and 110 and 111 each denote a low-pass filter.

Figure 1:
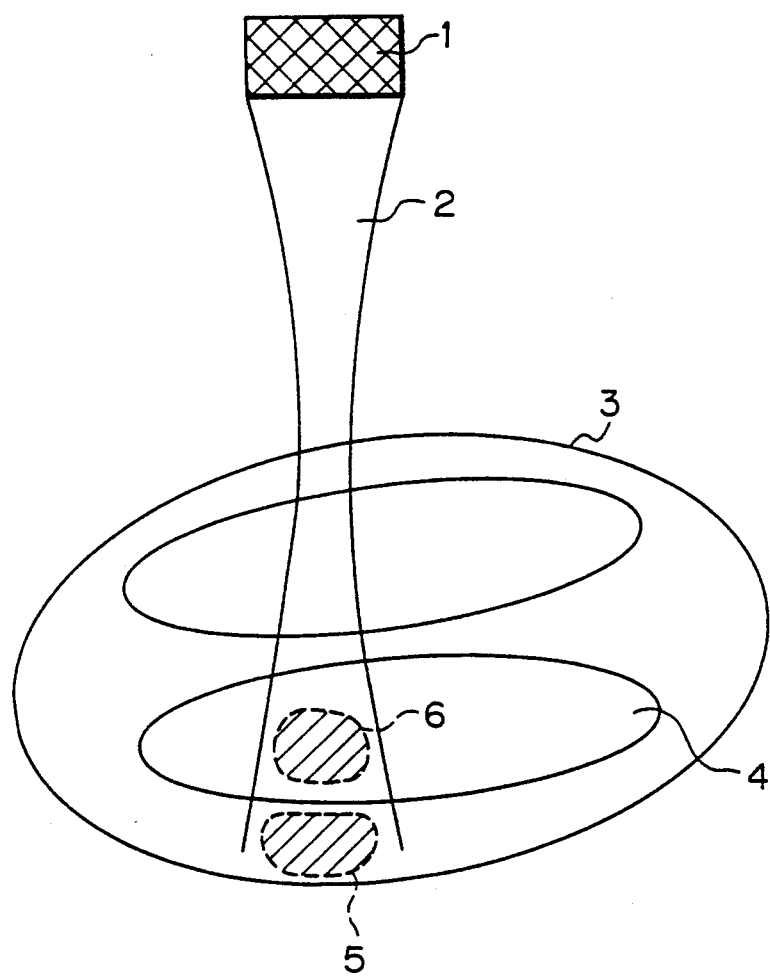
FIG. 1 is a diagram indicating a construction for obtaining a backscattering power of a tissue by using the blood backscattering power in the vicinity of the tissue, as a reference.
Figure 2:
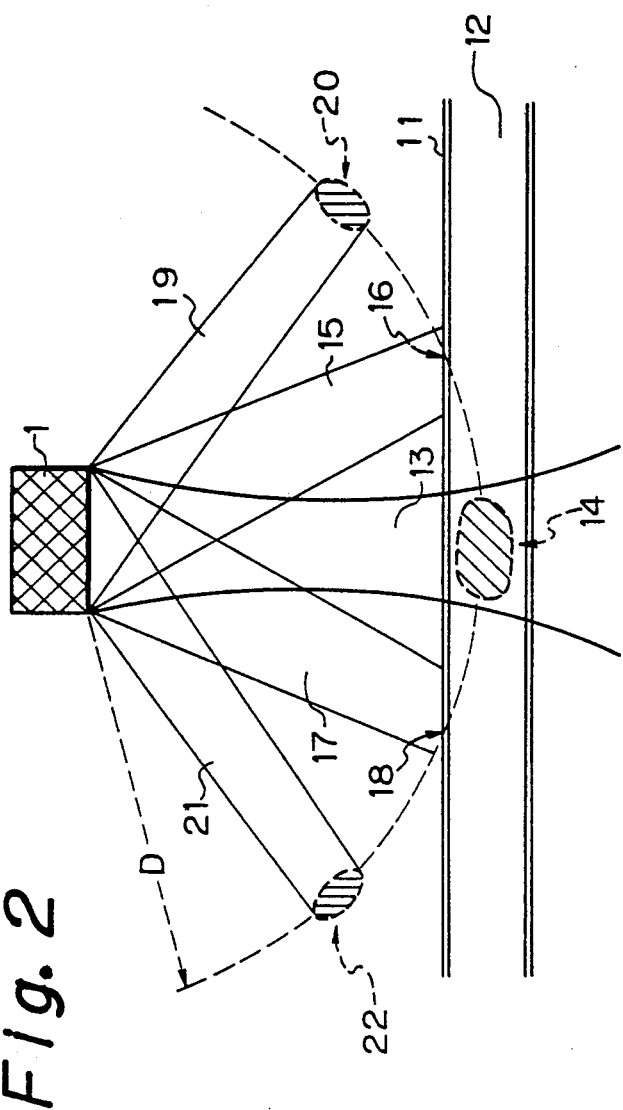
FIG. 2 is a diagram showing causes of clutters components superimposed on ultrasound signals which have been generated by blood backscattering.

Although not shown, it is assumed that all the constructions for obtaining a blood backscattering power which are explained in this specification, are used with (being connected to) or incorporated in a general ultrasonic diagnosing apparatus (ultrasonograph). As being well known, such an ultrasonic diagnosing apparatus comprises an oscillator for generating a high frequency signal corresponding to a frequency of an ultrasound signal; an ultrasonic transducer for converting an electric signal of the above high frequency to an ultrasound signal, transmitting the ultrasound signal into a human body, receiving ultrasound signals which are generated in various portions in the human body by reflecting or backscattering the above transmitted ultrasound signal, and converting the received ultrasound signals to electric signals, respectively; a timing generator for determining cyclic timing of the above transmitting of the ultrasound signal into the human body; and a delay for determining delay timing from the above cyclic timing, where the delay timing corresponds to a specific depth in the human body, a specific distance from the ultrasonic transducer and an objective portion of the human body located at the above depth. Thus, an electric signal which is converted from an ultrasound signal which has been generated in a specific depth, i.e., the above depth, in the human body by reflecting or backscattering the transmitted cyclic ultrasound signals, can be obtained, and it is assumed that input signals of quadrature detector units in the constructions of FIGS. 3, 6, 9, 11, 13, 15, and 18, are electric signals converted from ultrasound signals which have been generated in a specific range of depths in the human body by reflecting or backscattering the transmitted cyclic ultrasound signals, and the specific range is preset corresponding to a position of blood for which obtaining a blood backscattering power is desired, as shown with reference 5 in FIG. 1 and reference 14 in FIG. 2.

In the construction of FIG. 3, the above input signal is input into the quadrature detector unit 100. Since the input signal is converted from the above ultrasound signal, the input signal is modulated with a high frequency signal which is the same as the frequency of the ultrasound signal. In the quadrature detector unit 100, the multiplier 108 multiplies the input signal by a high frequency signal of the form $\cos\omega t$, and the multiplier 109 multiplies the input signal by another high frequency signal of the form $\sin\omega t$. Both the high frequency signals are generated in a high frequency oscillator (not shown, this oscillator may be the same type oscillator as the above-mentioned oscillator in the ultrasonic diagnosing apparatus) where the frequency is equal to the frequency of the ultrasound signal, and the phase of the signal $\cos\omega t$ precedes the phase of the signal $\sin\omega t$ by 90 degrees. The outputs of the multipliers 108 and 109 are respectively input into the low-pass filters 110 and 111. Thus, the above input signal is demodulated in the quadrature detector unit 100, a real part of the demodulated signal is output from the low-pass filter 110, and an imaginary part of the demodulated signal is output from the low-pass filter 111.

Figure 4:
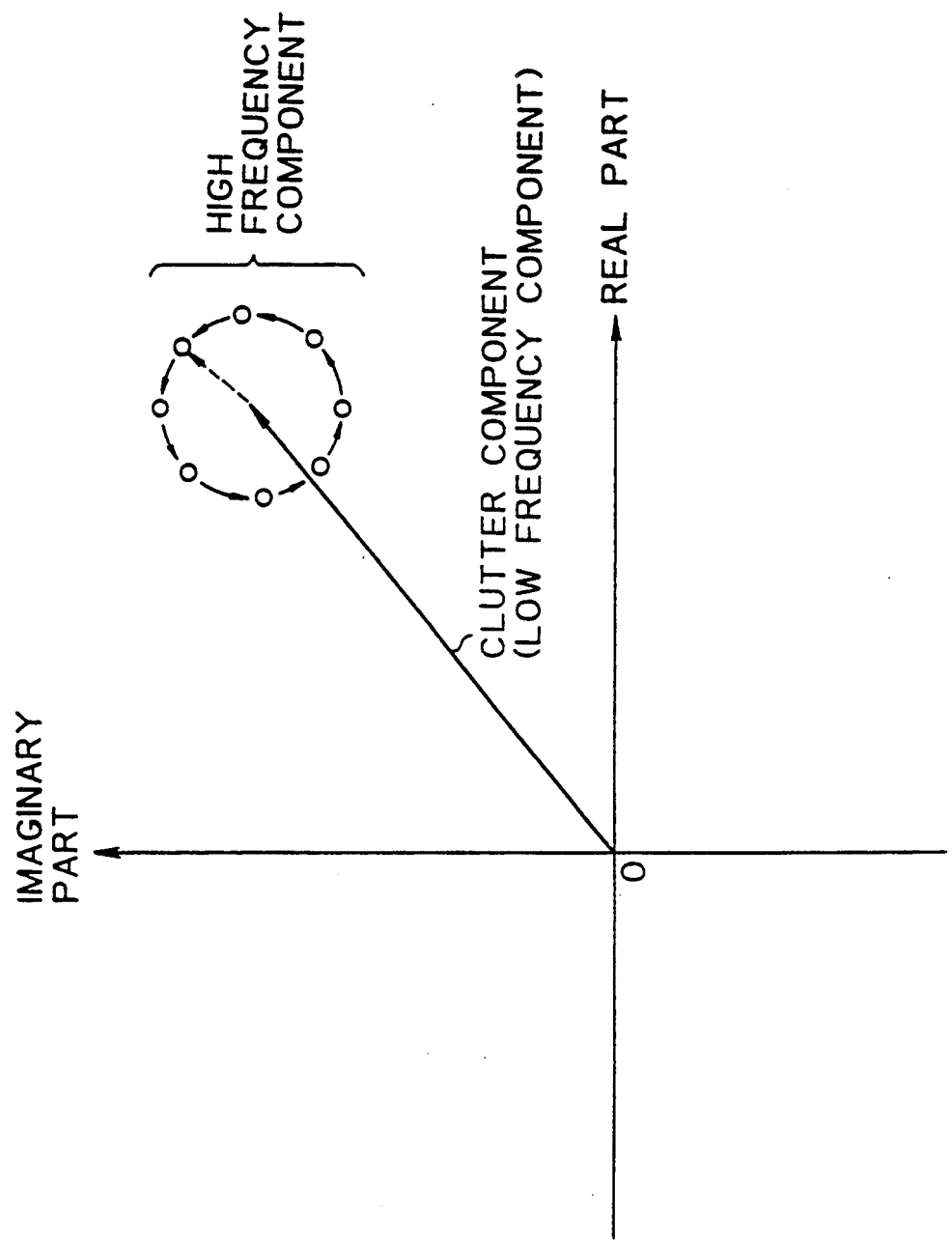
FIG. 4 is a diagram showing real and imaginary parts of demodulated input signals which are converted from ultrasound signals including signals due to the blood backscattering.

FIG. 4 is a diagram showing a typical example of the real and imaginary parts of the above demodulated signal. As shown in FIG. 4, the above demodulated signal is comprised of the sum of a low-frequency clutter component and a high frequency component. The low-frequency clutter component is comprised of the sum of the aforementioned clutter components generated by reflection of the side lobe beams at boundaries of different tissues, or backscattering of the side lobe beams in some tissues which are not of interest, where the boundaries and the tissues are each located at a position of the same propagation delay, i.e., distance from the ultrasonic transducer as the position at which the blood backscattering occurs. Since the tissues in a human body, in particular tissues of a heart or a blood vessel vibrate with a low frequency, typically synchronized with the pulsation, the above clutter component varies with a low frequency. On the other hand, since the blood flows, the ultrasound signals generated by backscattering from blood cells which move very fast (a typical maximum velocity is about 2 m/sec) vary rapidly, i.e., with a much higher frequency. Namely, the above high frequency component shown in FIG. 4 corresponds to the ultrasound signals due to the blood backscattering.

In the construction of FIG. 3, the above outputs of the quadrature detector unit 100 are respectively converted to digital signals in the sample & hold circuits 101 and 102, and then, the digital signals are respectively input into the high-pass filters 103 and 104. The high-pass filters 103 and 104 are provided for removing the above-mentioned low-frequency clutter component from each of the digital signals corresponding to the real and imaginary parts of the above demodulated input signals. After removing the low-frequency clutter component, the above digital signals corresponding to the real and imaginary parts of the demodulated input signals are respectively squared in the square calculating units 105 and 106, and then, the squared real and imaginary parts are summed in the adder 107 to obtain the blood backscattering power. In the construction of FIG. 3, the operations which occur in, and after, the high-pass filters 103 and 104 are realized by a digital signal processor.

Figure 5A:
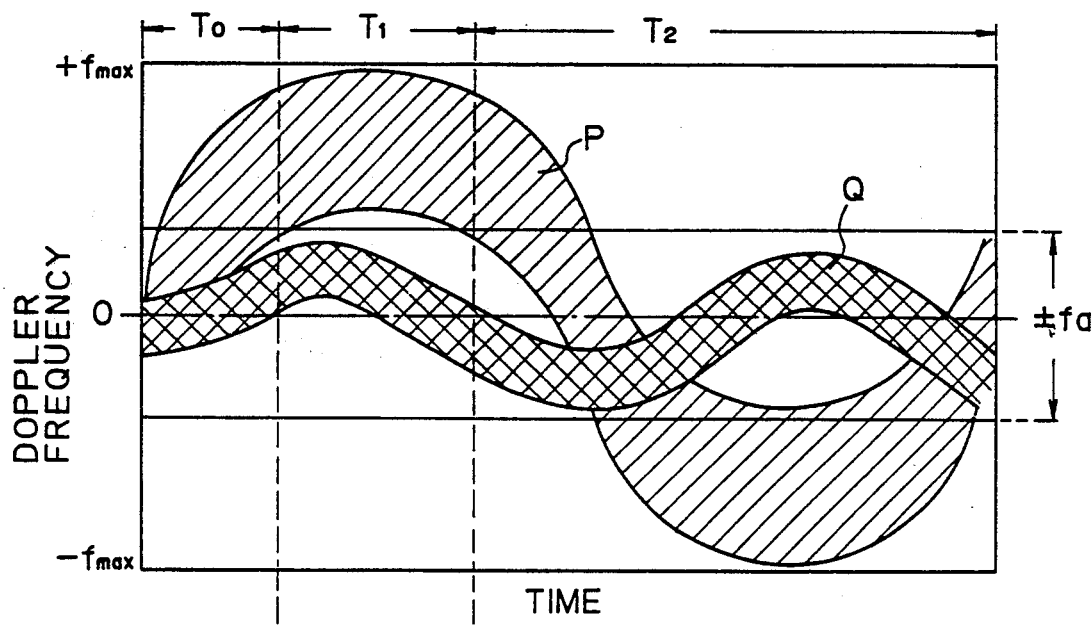
FIG. 5A is a diagram showing an example of a Doppler spectrum of intensity of the demodulated input signal converted from ultrasound signals including signals due to the blood backscattering.

FIG. 5A is a diagram showing an example of a Doppler spectrum of the intensity of the demodulated input signal which is converted from ultrasound signals including signals due to the blood backscattering. In FIG. 5A, the ordinate corresponds to a Doppler frequency, the abscissa corresponds to time, and a distribution of the intensity of the above demodulated signal on a two-dimensional plane of the Doppler frequency versus time, is shown. The Doppler frequency is obtained by Fourier transformation of the sampled digital which are in the outputs of the sample & hold circuits 101 and 102. As explained later, the Fourier transformation of the sampled digital signals is carried out by inputting a predetermined number of successive samples into a fast Fourier transforming unit at each sampling cycle. The Doppler frequency is known as a quantity indicating a velocity component in the direction of the ultrasonic wave beam, of the object which backscatters an ultrasound signal.

In the distribution of the intensity shown in FIG. 5A, areas wherein the intensity is relatively enhanced are indicated by hatching. As shown in FIG. 5A, two types of continuously enhanced areas (respectively denoted by P and Q) appear in the Doppler spectrum. The ranges of the Doppler frequency of the continuous areas P and Q respectively vary between the positive region and the negative region of the Doppler frequency, cyclically on the whole. The cycles of the variations of the ranges of the Doppler frequency of both the areas P and Q appear to be the same, and the cycle corresponds to the pulsation. The range of the area P varies with a relatively large amplitude of the Doppler frequency, and the range of the area Q varies with a relatively small amplitude of the Doppler frequency. In addition, the intensity in the area P is relatively small, and the intensity in the area Q is relatively large. The area P corresponds to signal components due to the backscattering of input signals by the blood cells, and the area Q corresponds to the clutter components. The above large amplitude of the range of the Doppler frequency is due to the fast flow of the blood cells and the change of the direction of the flow is due to the pulsation. The variation of the range of the area Q with a relatively small amplitude corresponds to the above-mentioned vibration of other tissues with a low frequency. The provision of the high-pass filters 103 and 104 in the construction of FIG. 3 substantially eliminates the digital signal components in the regions where the absolute value of the Doppler frequency is not more than a predetermined cutting frequency $f_a$, as indicated in FIG. 5A.

Figure 5B:
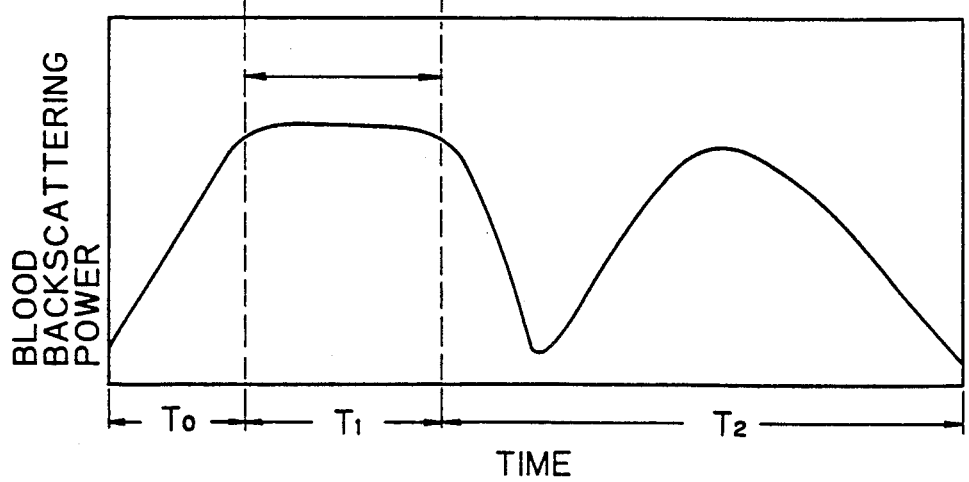
FIG. 5B is a diagram showing an example of a spectrum of blood backscattering power obtained by the construction of FIG. 3.

However, the above-mentioned process of uniformly eliminating the low-frequency (low Doppler frequency) components with a constant cutting frequency $f_a$ also reduce the signal components due to blood backscattering because considerable portions of the above area P are included in the above uniformly eliminated region as shown in FIG. 5A. Although it is described in the above that the amplitude of the area Q is relatively small, this amplitude is too large when considering the above reduction in the signal components due to blood backscattering. The amplitude of the area Q is enhanced by an effect of reflections from some portions of tissue which move considerably fast, such as valves in a heart. Thus, the above cutting frequency $f_a$ must be set to a relatively high value, and therefore, the considerable reduction of the signal components due to blood backscattering cannot be avoided by the above provision of FIG. 3. Namely, the construction of FIG. 3 may provide a wrong value of the blood backscattering power, which is smaller than the true value of the blood backscattering power. FIG. 5B is a diagram showing an example of a spectrum of blood backscattering power obtained in the construction of FIG. 3 when setting the cutting frequency $f_a$ as shown in FIG. 5A. As indicated in FIG. 5B, the blood backscattering power is reduced, particularly in the time ranges denoted by $T_0$ and $T_2$.

FIRST EMBODIMENT (FIGS. 6, 7A, 7B, AND 8)

Figure 6:
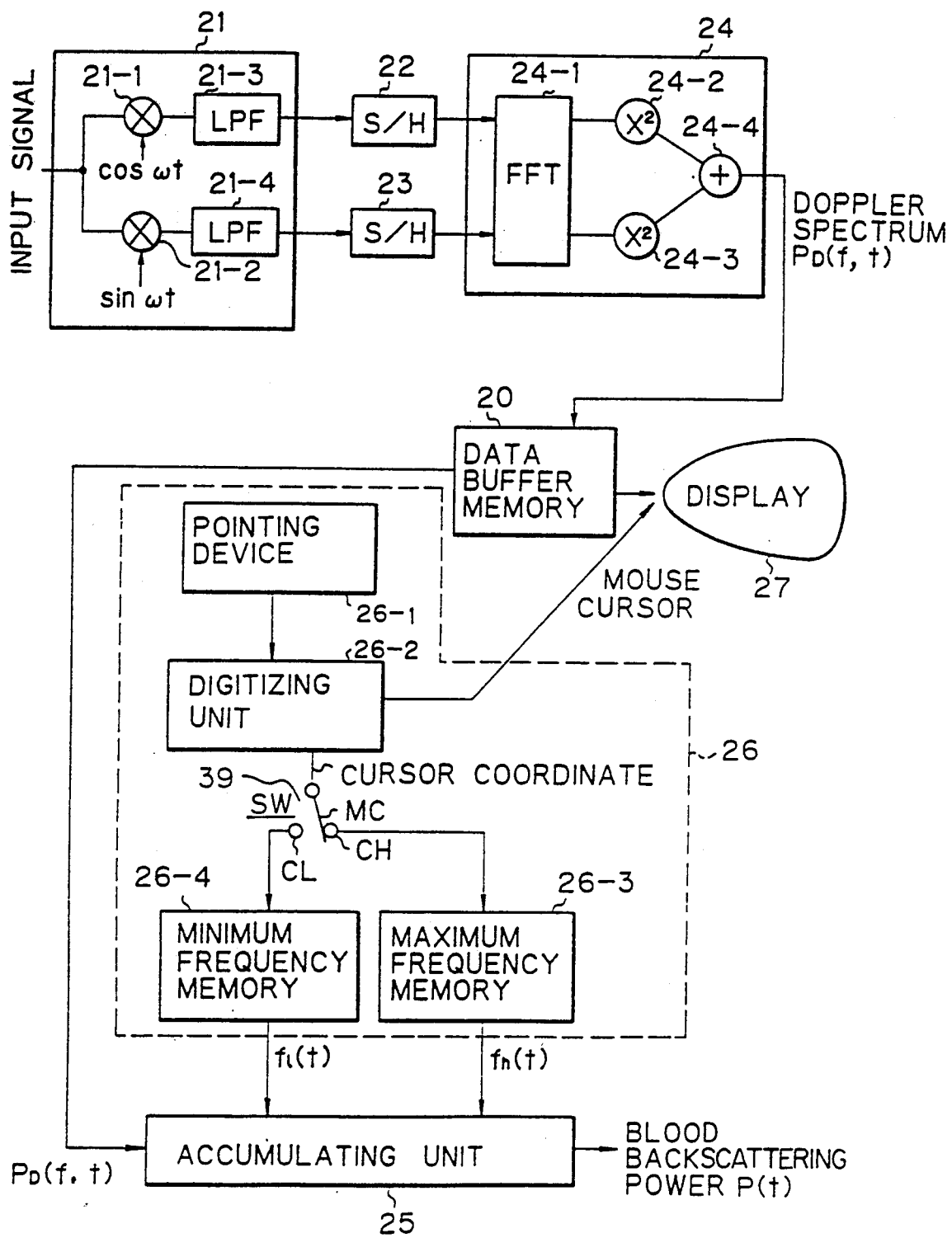
FIG. 6 is a diagram showing a construction of a first embodiment of the present invention.

FIG. 6 is a diagram showing a construction of a first embodiment of the present invention. In FIG. 6, reference numeral 20 denotes a data buffer memory, 21 denotes a quadrature detector unit, 22 and 23 each denote a sample and hold circuit, 24 denotes a Doppler spectrum calculating unit, 25 denotes an accumulating unit, 26 denotes a Doppler frequency range setting unit, and 27 denotes a display unit. In the quadrature detector unit 21, 21-1 and 21-2 each denote a multiplier, and 21-3 and 21-4 each denote a low-pass filter. In the Doppler spectrum calculating unit 24, 24-1 denotes a fast Fourier transforming unit, 24-2 and 24-3 each denote a square calculating unit, and 24-4 denotes an adder unit. In the Doppler frequency range setting unit 26, reference numeral 26-1 denotes a pointing device, 26-2 denotes a digitizing unit, 26-4 denotes a minimum frequency memory, 26-3 denotes a maximum frequency memory, and 39 denotes a switch unit.

The quadrature detector unit 21 and the sample & hold circuits 22 and 23 operate in the same way as the corresponding elements in the construction of FIG. 3. Thus the demodulated digital signals corresponding to the real and imaginary parts are input into the fast Fourier transforming unit 24-1 in the Doppler spectrum calculating unit 24. The fast Fourier transforming unit 24-1 Fourier transforms the real and imaginary parts of the digital signal to obtain distributions of the real and imaginary parts of the digital signal amplitude as a function of the Doppler frequency f and time t. The Fourier transformed real and imaginary parts of the digital signal amplitude are respectively squared in the square calculating units 24-2 and 24-3, and then, the squared real and imaginary parts are summed in the adder unit 24-4 to obtain a Doppler spectrum $P_D(f,t)$, which is a two-dimensional distribution, on a plane of the Doppler frequency f and the time t, i.e., a plot of frequency versus time of the intensity of the demodulated input signal which is converted from ultrasound signals including signals due to the blood backscattering. The data of the Doppler spectrum is temporarily held in the data buffer memory 20, and the Doppler spectrum is displayed by the display apparatus 27 in the construction of FIG. 6. In the display unit 27, shown a gray scale display is used. Namely, the intensity at each area on the plane of the Doppler frequency f and the time t, is displayed on a screen of the display unit 27 with a tone, i.e., brightness corresponding to the amount of the intensity at the area. Alternatively, the intensity at each area on the plane of the Doppler frequency f and the time t, may be displayed on a screen of the display unit 27, i.e., a color similar, with a hue corresponding to the amount of the intensity at the area, or the Doppler spectrum may be displayed on the plane of the Doppler frequency f and the time t, as a three-dimensional plot. Thus, an operator can recognize the above-mentioned areas P and Q according to tones or hues of these areas. Namely, the operator can recognize the area Q due to the clutter components based on the tone or hue of the area.

Figure 7A:
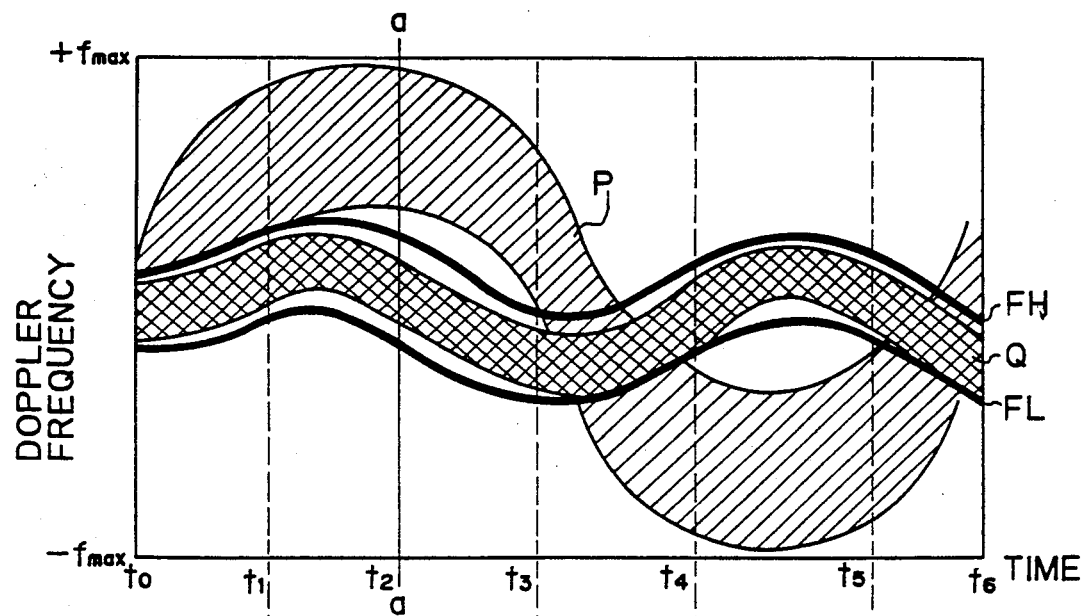
FIG. 7A is a diagram showing an example of a Doppler spectrum of the intensity of the demodulated input signal which is converted from ultrasound signals including signals due to the blood backscattering.

The Doppler frequency range setting unit 26 is provided to determine an arbitrary area of the above plane of the Doppler frequency f and the time t, for eliminating data of the Doppler spectrum on the above area Q due to the clutter components when calculating a blood backscattering power. During the determination of the area, the content of the data buffer memory 20 is not renewed, and the display of the Doppler spectrum on a screen of the display unit 27 is frozen. The area is manually input to the Doppler frequency range setting unit 26 by the pointing device 26-1. The pointing device 26-1 may be, for example, a mouse, a track ball, or the like. The input from the pointing device 26-1 is digitized to obtain coordinates of the mouse cursor or other pointing device. The coordinates of a mouse cursor are supplied to the display unit 27 to superimpose a trace of the i.e., a plot of frequency versus time cursor, on the Doppler spectrum on the display. FIG. 7A is a diagram showing an example Doppler spectrum of the intensity of the demodulated input signal which is converted from ultrasound signals including signal components due to the blood backscattering. In the example of FIG. 7A, boundaries of the above area are indicated by bold lines. These lines can be drawn, for example, by dragging the mouse. As indicated in FIG. 7A, an approximate minimum area including the above area Q due to the clutter components can be determined.

In addition, the Doppler frequency coordinate of the mouse cursor at each sampling time is memorized in the maximum frequency memory 26-3 while an operator inputs the boundary of the upper side of the above area, and the Doppler frequency coordinate of the mouse cursor at each sampling time is memorized in the minimum frequency memory 26-4 while an operator inputs the boundary of the lower side of the above area. The switch 39 connects the digitizing unit 26-2 to either of the maximum and minimum frequency memories 26-3 and 26-4, according to which of the boundaries on the upper and lower sides are being input. This switch 39 may be realized by a manual switch, or by a program wherein the operation is switched from one to another of the inputs of the boundaries on the upper and lower sides according to a predetermined command input, for example, a key stroke from a keyboard. Thus, the above boundaries on the upper and lower sides are memorized in the maximum and minimum frequency memories 26-3 and 26-4 as functions $f_h(t)$ and $f_l(t)$ of time t, respectively.

After the above input of the boundaries are completed, the data of the Doppler spectrum except the data in the above eliminated area, is accumulated in the accumulating unit 25 to obtain the blood backscattering power in the duration wherein the above boundaries have been input in the Doppler frequency range setting unit 26.

FIG. 8 is a diagram showing an example construction of the accumulating unit 25 in the construction of FIG. 6. In FIG. 8, reference numeral 25-1 denotes a gate control unit, 25-2 denotes a gate, 25-3 denotes an adder, and 25-4 denotes a register. The gate control unit 25-1 reads the above data of the boundaries $f_h(t)$ and $f_l(t)$ of each time t from the maximum and minimum frequency memories 26-3 and 26-4, outputs an active gate control signal to the gate 25-2 to make the gate 25-2 open when the Doppler frequency f of the data of the Doppler spectrum PD(f,t) which is currently input into the gate 25-2, does not satisfy the condition, $f_1(t) \leq f \leq f_h(t)$, and outputs an inactive gate control signal to make the gate 25-2 close when the Doppler frequency f of the data of the Doppler spectrum PD(f,t) which is currently input into the gate 25-2, satisfies the above condition. Thus, only the data of the Doppler spectrum PD(f,t) where the Doppler frequency f does not satisfy the condition, $f_1(t) \leq f \leq f_h(t)$, is supplied to one of two input terminals of the adder 25-3. The adder 25-3 obtains a sum of the two inputs, and the output of the adder 25-3 is applied to the register 25-4. The output of the register 25-4 is applied to the other input terminal of the adder 25-3. Thus, the data of the Doppler spectrum $P_D$(f,t) where the Doppler frequency f does not satisfy the condition, $f_1(t) \leq f \leq f_h(t)$, is accumulated in the accumulating unit 25. The accumulation is carried out for each time t to obtain the blood backscattering power P(t). Namely, the obtained blood backscattering power P(t) is expressed as $$P(t) = \sum_{f=-f_{max}}^{f_1(t)} P_D(f,t) + \sum_{f=f_h(t)}^{f_{max}} P_D(f,t),$$

where $f_{max}$ and $-f_{max}$ are respectively maximum and minimum of the Doppler frequency in the Doppler spectrum obtained in the embodiment.

Figure 7B:
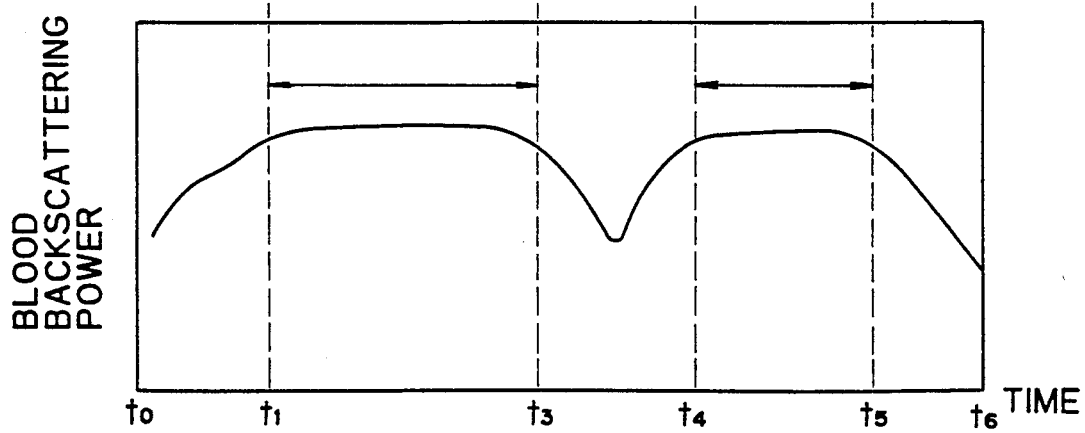
FIG. 7B is a diagram showing an example of a spectrum of blood backscattering power obtained by the construction of FIG. 6.

FIG. 7B is a diagram showing an example of the blood backscattering power obtained by the construction of FIG. 6. As shown in FIGS. 7A and 7B, the loss in the data in the area P can be minimized, and therefore, a more accurate value for the blood backscattering power can be obtained by the construction of FIG. 6 than the construction of FIG. 3. In particular, values of the blood backscattering power in the sections $t_1$ to $t_3$, and $t_4$ to $t_5$, are accurate because no portion in these sections is removed in the above calculation as indicated in FIG. 7A.

SECOND EMBODIMENTS (FIGS. 9, AND 10)

Figure 9:
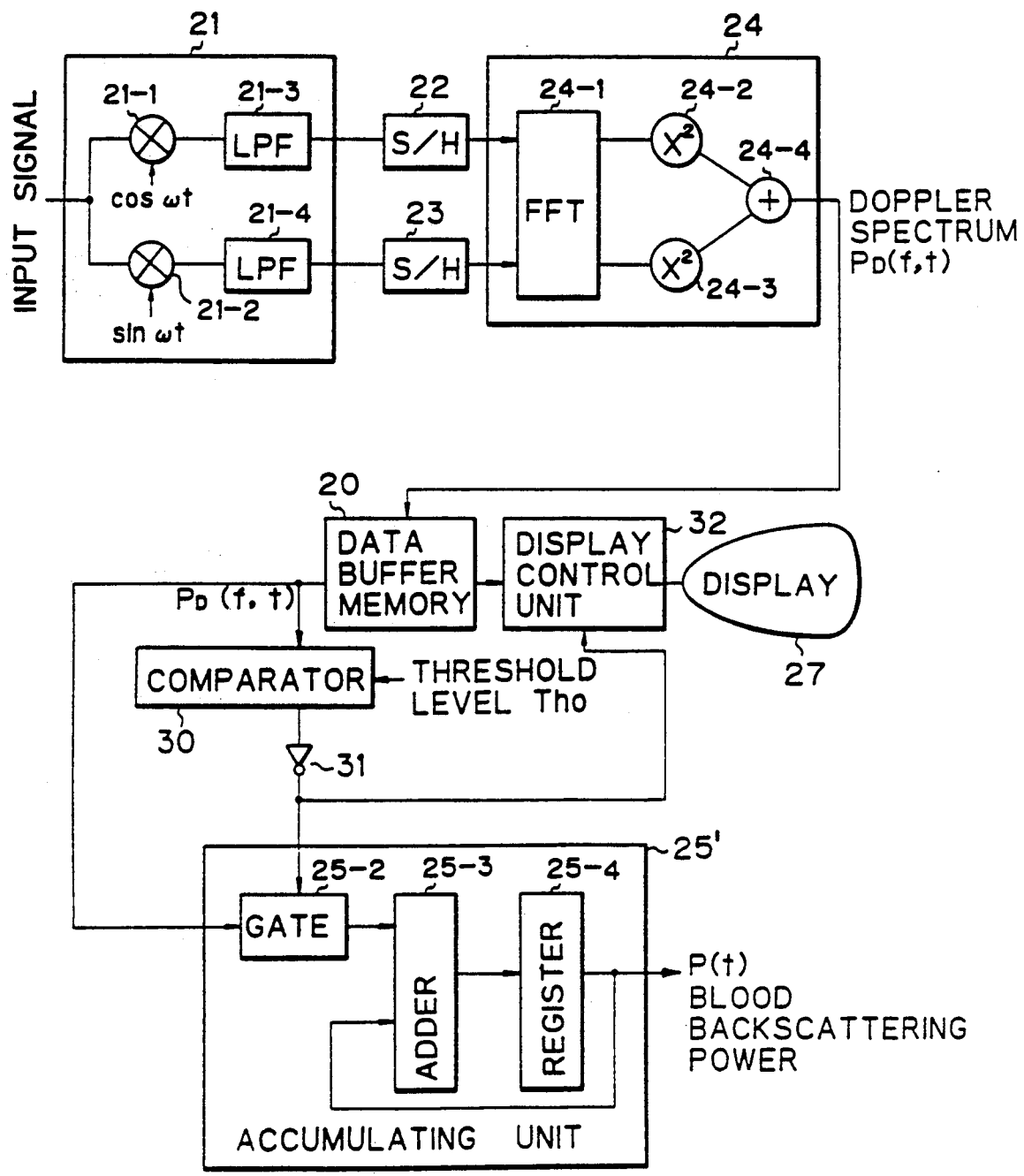
FIG. 9 is a diagram showing a construction of a second embodiment of the present invention.

FIG. 9 is a diagram showing a construction of a second embodiment of the present invention. In FIG. 9, reference numeral 25' denotes an accumulating unit, 30 denotes a comparator, 31 denotes an inverter, and 32 denotes a display control unit. In the accumulating unit 25', reference numeral 25-2 denotes a gate, 25-3 denotes an adder, and 25-4 denotes a register. The construction of the accumulating unit 25' operates in the same way as a portion of the construction of FIG. 8 except the gate control unit 25-1. In FIG. 9, the data buffer memory 20, the quadrature detector unit 21, the sample and hold circuits 22 and 23, the Doppler spectrum calculating unit 24, and the display unit 27, are the same as the corresponding constructions in FIG. 6.

In the construction of FIG. 9, the comparator 30 compares each value $P_D$(f,t) of the Doppler spectrum with a threshold value Th which is set in advance so that the clutter components which correspond to large values of the Doppler spectrum $P_D$(f,t), can be discriminated from the components due to the blood backscattering, i.e., smaller values. FIG. 10 is a diagram of a Doppler spectrum at a certain time for explaining the operation of the construction of FIG. 9. As shown in FIG. 10, the clutter components can be effectively eliminated when the threshold value $Th_0$ is appropriately preset.

The output of the comparator 30 is supplied through the inverter 31 to the gate 25-2 in the accumulating unit 25' so that the output of the inverter 31 supplies an active gate control signal to the gate 25-2 to make the gate 25-2 open when the value $P_D$(f,t) of the Doppler spectrum currently input into the gate 25-2, is less than the above threshold value $Th_0$, and the output of the inverter 31 supplies an inactive gate control signal to make the gate 25-2 close when the value of the Doppler spectrum PD(f,t) which is currently input into the gate 25-2, is not less than the above threshold value $Th_0$. Thus, only the data of the Doppler spectrum PD(f,t) which is less than the threshold value $Th_0$, is supplied to one of two input terminals of the adder 25-3. Thus, the data of the Doppler spectrum $P_D$(f,t) which is less than the threshold value $Th_0$, is accumulated in the accumulating unit 25'. The accumulation is carried out for each time t to obtain the blood backscattering power P(t). Namely, the obtained blood backscattering power P(t) is expressed as $$P(t) = \sum_{P_D(f,t) < Th_0} P_D(f,t).$$

In the construction of FIG. 9, the output of the inverter 31 is also supplied to the display control unit 32. The display control unit 32 modifies the data of the Doppler spectrum which is to be supplied from the data buffer memory 20 to the display unit 27, so that the data of the Doppler spectrum not less than the above threshold value $Th_0$ is not displayed on the screen of the display unit 27.

According to the second embodiment of the present invention, the clutter components can be automatically eliminated without freezing the data of the Doppler spectrum and manually inputting the boundaries of the area of the elimination.

THIRD EMBODIMENT (FIGS. 11, AND 12)

Figure 11:
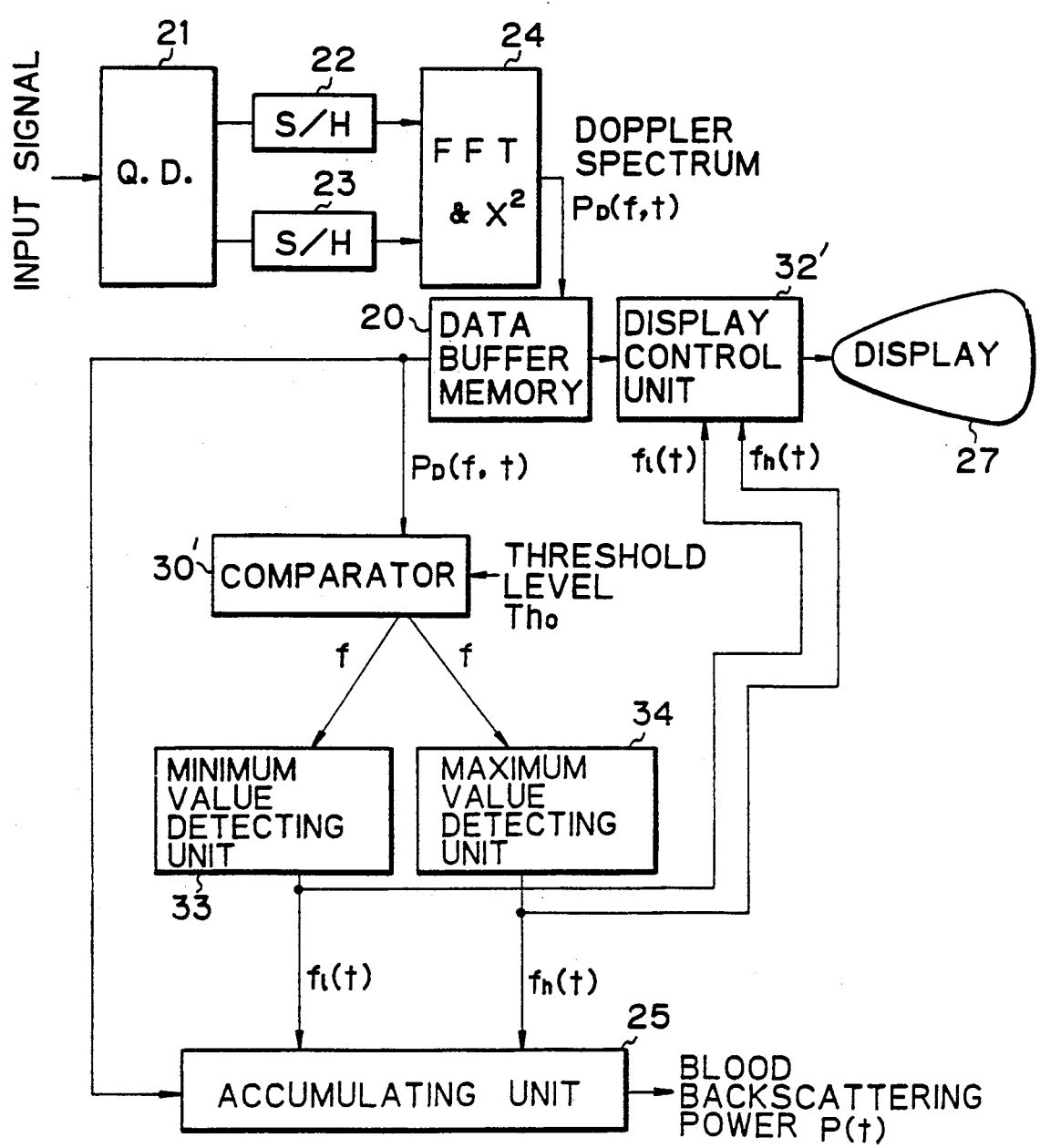
FIG. 11 is a diagram showing a construction of a third embodiment of the present invention.

FIG. 11 is a diagram showing a construction of a third embodiment of the present invention. Since the above-mentioned operation of the fast Fourier transforming unit 24 is carried out using a limited number (for example, 128) of successively sampled values which are output from the sample and hold circuits 22 and 23, in practice the distribution curve $P_D$(f,t) of the Doppler spectrum at each sampling time t is not simple and smooth as shown in FIG. 10. The distribution curve $P_D$(f,t) may have some valleys, and the valleys may be located near the above threshold value $Th_0$ of the second embodiment, as shown in FIG. 12. FIG. 12 is a diagram indicating a Doppler spectrum at a certain time for explaining the operation of the construction of FIG. 11. The existence of the valleys is taken into account in the construction of FIG. 12.

In FIG. 11, reference numeral 30' denotes a comparator, 32' denotes a display control unit, 33 denotes a minimum value detecting unit, and 34 denotes a maximum value detecting unit. In FIG. 11, the data buffer memory 20, the quadrature detector unit 21, the sample and hold circuits 22 and 23, the Doppler spectrum calculating unit 24, and the display unit 27, are the same as the corresponding constructions in FIG. 9, and the construction of the accumulating unit 25 is the same as the construction of FIG. 8.

The operation of the construction of FIG. 11 is explained below. First, the boundaries outlining an area where data $P_D$(f,t) of the Doppler spectrum in that area is to be eliminated for excluding the clutter components in calculating the blood backscattering power, are determined, where it is assumed that the data $P_D$(f,t) of the Doppler spectrum at each time t is supplied to the comparator 30' in the order of the Doppler frequency f from the minimum $-f_{max}$ to the maximum $f_{max}$.

The comparator 30' compares each value $P_D(f,t)$ of the Doppler spectrum with a threshold value $Th_0$, which is set thereto in advance, so that the clutter components which correspond to large values of the Doppler spectrum $P_D(f,t)$, can be discriminated from the components due to the blood backscattering, as indicated in FIG. 12. The result of the comparison is supplied to the minimum value detecting unit 33 and the maximum value detecting unit 34. The minimum value detecting unit 33 stores a Doppler frequency of data $P_D(f,t)$ of the Doppler spectrum at each sampling time t, as a minimum boundary frequency $f_1(t)$, when the data $P_D(f,t)$ is data which first becomes not less than the threshold value $Th_0$, from the data $P_D(-f_{max},t)$. The maximum value detecting unit 34 renews the content thereof with a Doppler frequency f corresponding to the data $P_D(f,t)$ which causes a current output of the comparator 30' when the output of the comparator 30' determines that the data $P_D(f,t)$ is not less than the threshold value $Th_0$, i.e., stores as a maximum boundary frequency, the frequency at which the data PD(f,t) last becomes smaller than the threshold level $TH_0$. Since, in practice, the data of the Doppler spectrum at each sampling time t is read out from the data buffer memory 20 in response to corresponding addresses of the data buffer memory 20 the addresses of which are generated by an address generator (not shown), the minimum value detecting unit 33 and the maximum value detecting unit 34 can recognize the above Doppler frequencies based on these addresses. Thus, the minimum value detecting unit 33 can obtain the boundary $f_1(t)$ on the lower side of the area for eliminating the clutter components, and the maximum value detecting unit 34 can obtain the boundary $f_h(t)$ on the upper side of the area. The boundaries $f_h(t)$ and $f_1(t)$ on the upper and lower sides are supplied to the accumulating unit 25 and the display control unit 32'. As readily understood from symmetry, when the data $P_D(f,t)$ of the Doppler spectrum at each time t is supplied to the comparator 30' in the order of the Doppler frequency f from the maximum $f_{max}$ to the minimum $-f_{max}$, the above operations of the minimum value detecting unit 33 and the maximum value detecting unit 34 must be replaced with each other.

The accumulating unit 25 obtains the blood backscattering power P(t) in the same way as the accumulating unit 25 of FIG. 8. Namely, $$P(t) = \sum_{f=-f_{max}}^{f_1(t)} P_D(f,t) + \sum_{f=f_h(t)}^{f_{max}} P_D(f,t),$$

is obtained. The display control unit 32' modifies the data of the Doppler spectrum which is to be supplied from the data buffer memory 20 through the display control unit 32' to the display unit 27, so that the data of the Doppler spectrum which is within the above area from $f_1(t)$ to $f_h(t)$ is not displayed on the screen of the display unit 27.

FOURTH EMBODIMENT (FIGS. 13, AND 14)

Figure 13:
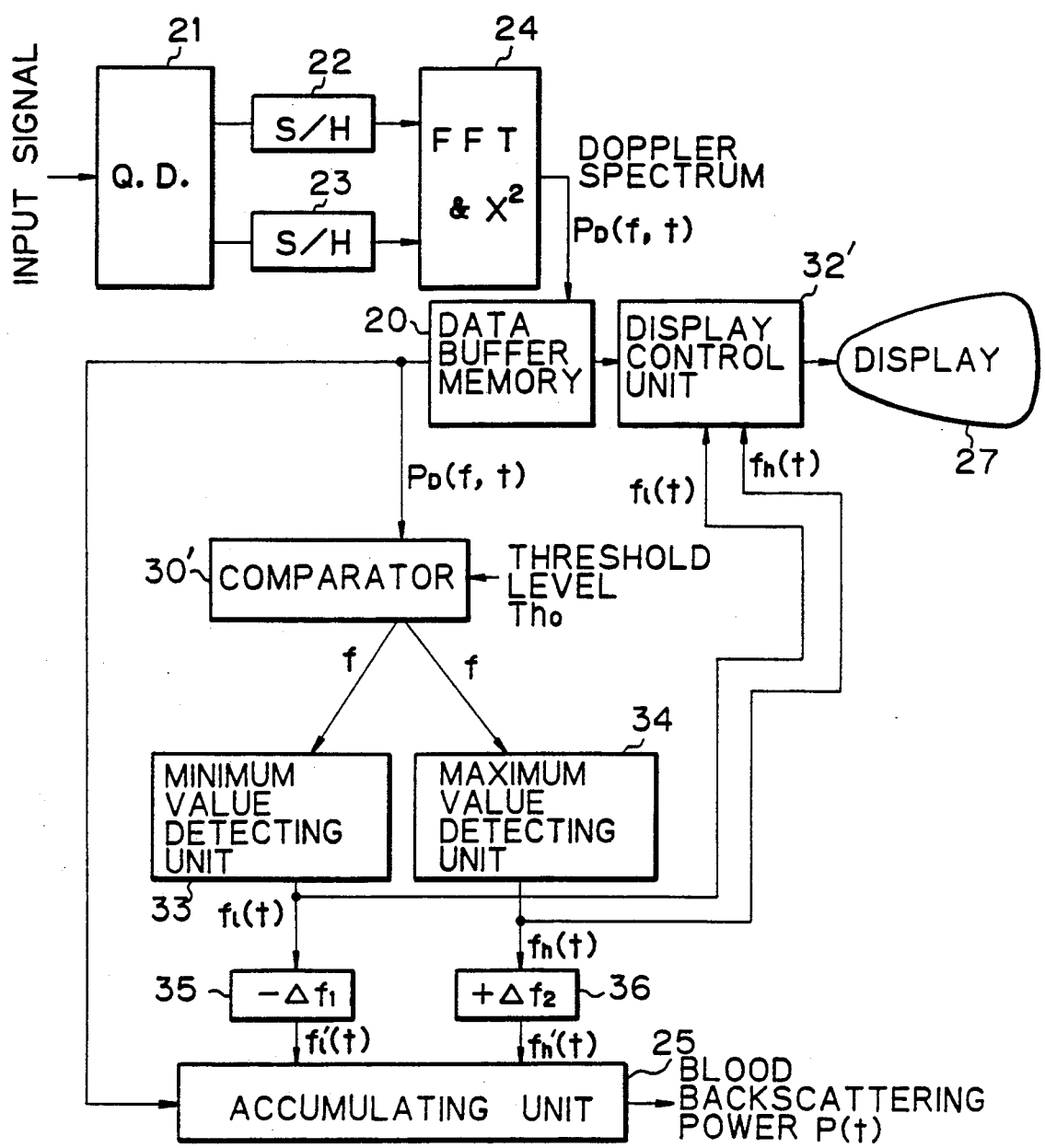
FIG. 13 is a diagram showing a construction of a fourth embodiment of the present invention.

FIG. 13 is a diagram showing a construction of a fourth embodiment of the present invention. Although the data of the Doppler spectrum which is larger than the threshold value $Th_0$ is eliminated when calculating the blood backscattering power in the second and third embodiments, the Doppler spectrum still contains slope portions of the clutter components on the both sides of the area wherein the data of the Doppler spectrum is eliminated as above in the second and third embodiments, as indicated by $\Delta f_1$ and $\Delta f_2$ in FIG. 14. FIG. 14 is a diagram of a Doppler spectrum at a certain time for explaining the operation of the construction of FIG. 13. This problem, i.e., the remaining slope portions is taken into account in the construction of FIG. 13.

In FIG. 13, reference numeral 35 denotes a minimum value modifying unit, and 36 denotes a maximum value modifying unit. All the other elements in FIG. 13 are respectively the same as the corresponding elements in FIG. 11. The minimum value modifying unit 35 decreases each output value $f_1(t)$ of the minimum value detecting unit 33, by an estimated width $\Delta f_1$ of the slope portion on the lower side of the area wherein the above data of the Doppler spectrum is eliminated. The maximum value modifying unit 36 increases each output value $f_h(t)$ of the maximum value detecting unit 34, an estimated width $\Delta f_2$ of the other slope portion, i.e., the slope portion, on the upper side of the area wherein the above data of the Doppler spectrum is eliminated. Thus, the minimum value modifying unit 35 outputs a value $f_1'(t) = f_1(t) - \Delta f_1$ to the accumulating unit 25 as a boundary value on the lower side of the area wherein the data of the Doppler spectrum is eliminated, and the maximum value modifying unit 36 outputs a value $f_h'(t) = f_h(t) + \Delta f_2$ to the accumulating unit 25 as a boundary value on the upper side of the area wherein the data of the Doppler spectrum is eliminated.

The above widths $\Delta f_1$ and $\Delta f_2$ may be estimated in advance by experiment, or may be estimated according to the shape of the peak of the Doppler spectrum, corresponding to the clutter components at each sampling time t. In the latter method, the estimation, the peak may be approximated to a triangle, or a Gaussian distribution. When a triangle approximation is employed, the widths $\Delta f_1$ and $\Delta f_2$ are obtained based on similarity of a triangle corresponding to the peak above the threshold level $Th_0$ and a triangle corresponding to the whole peak. When the approximation to a Gaussian distribution is employed, for example, a width to $\pm \sigma$ may be considered as a total width of the peak, where $\sigma$ is a dispersion of the Gaussian distribution.

The above decreased boundary value $f_1'(t)$ and the increased boundary value $f_h'(t)$ are supplied to the accumulating unit 25. The accumulation in the accumulating unit 25 is carried out in the same way as explained with reference to FIG. 8 except that the above modified boundary values $f_1'(t)$ and $f_h'(t)$ are used instead of the aforementioned boundary values $f_1(t)$ and $f(t)$, respectively. Namely, the blood backscattering power P(t) is obtained as $$P(t) = \sum_{f=-f_{max}}^{f_1'(t)} P_D(f,t) + \sum_{f=f_h'(t)}^{f_{max}} P_D(f,t).$$

Thus, according to the construction of FIG. 13, almost all the clutter components can be eliminated in the calculation of the blood backscattering power. Wf, Wf1, and Wf2 as shown in FIGS. 10, 12 and 14, respectively, are the widths of the eliminated frequencies.

FIFTH EMBODIMENT (FIGS. 15, 16, AND 17)

Figure 15:
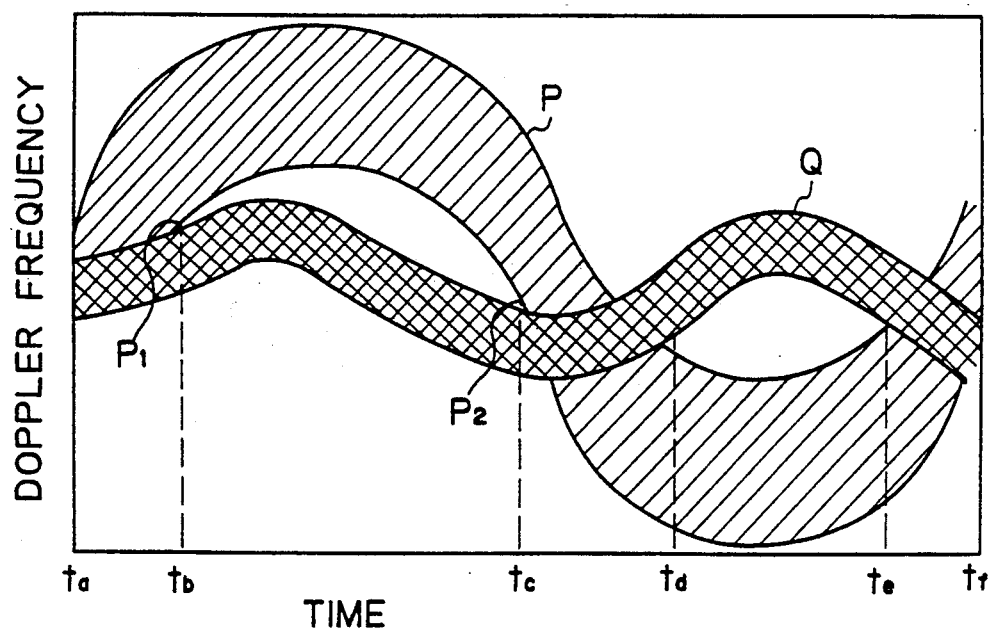
FIG. 15 is a diagram showing a Doppler spectrum for explaining the operation of the construction of the fifth embodiment of the present invention.

Since there may be some fluctuation in the values of the blood backscattering power as obtained above, it is desirable to obtain an average of a plurality of values of the blood backscattering power. FIG. 15 is a diagram indicating a Doppler spectrum for explaining the operation of the construction of the fifth embodiment of the present invention. As shown in FIG. 15, the area P corresponding to the blood backscattering is superimposed on the area Q corresponding to the clutter components in some sections of time ($t_a$ to $t_b$, $t_c$ to $t_d$, and $t_e$ to $t_f$), and the area P corresponding to the blood backscattering is hot superimposed on the area Q corresponding to the clutter components in other sections of time ($t_b$ to $t_c$, and $t_d$ to $t_e$). According to the above-mentioned first to fourth embodiments, the obtained blood backscattering powers are reduced in the above sections of time where the area P corresponding to the blood backscattering is superimposed on the area Q corresponding to the clutter components, as typically shown in FIG. 7B. Therefore, the above average must be calculated from the values of the blood backscattering power in the sections of time where the area P corresponding to the blood backscattering is not superimposed on the area Q corresponding to the clutter components Such an average can be obtained by the construction of FIG. 16 according to the fifth embodiment of the present invention.

Figure 16:
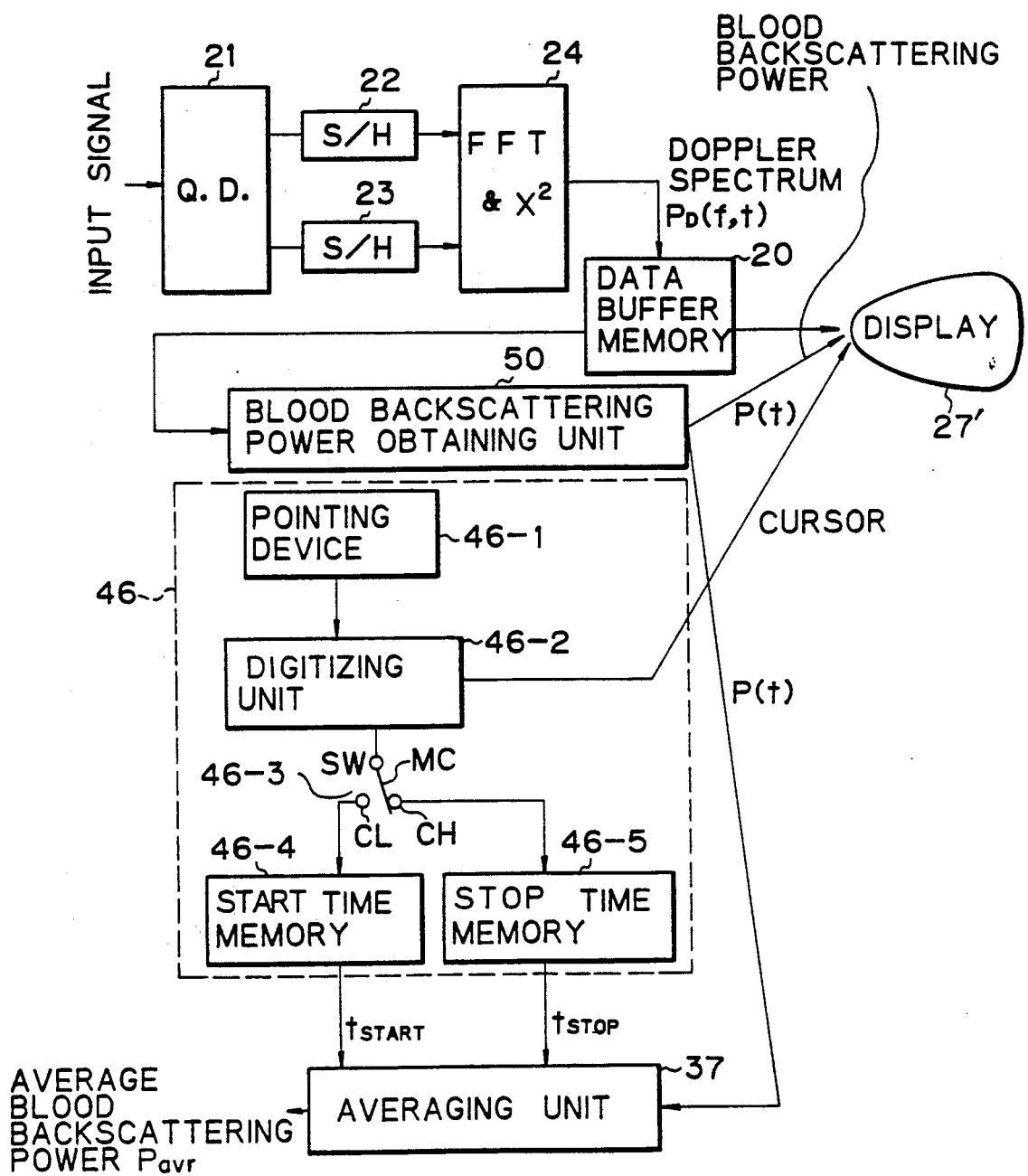
FIG. 16 is a diagram showing a construction of a fifth embodiment of the present invention.

FIG. 16 is a diagram showing a construction of a fifth embodiment of the present invention. In FIG. 16, reference numeral 27' denotes a display unit, 37 denotes an averaging unit, 46 denotes an averaging section setting unit, 46-1 denotes a pointing device, 46-2 denotes a digitizing unit, 46-3 denotes a switch unit, 46-4 denotes a start time memory, 46-5 denotes a stop time memory, and 50 denotes a blood backscattering power obtaining unit. In FIG. 16, the construction comprised of the data buffer memory 20, the quadrature detector unit 21, the sampler and hold circuits 22 and 23, the Doppler spectrum calculating unit 24, the display unit 27', and the blood backscattering power obtaining unit 50, corresponds to any of the constructions of FIGS. 6, 9, 11, and 13. Namely, the blood backscattering power obtaining unit 50 represents any of the constructions of FIGS. 6, 9, 11, and 13 and could include all elements shown in any one of those figures except the data buffer memory 20, the quadrature detector unit 21, the sample & hold circuits 22 and 23, the Doppler spectrum calculating unit 24, and the display unit 27', and the display unit 27' represents the display unit 27 and the display control unit 32 or 32' in the constructions of FIGS. 9, 11, and 13, except that the display unit 27' further functions as explained below.

The averaging section setting unit 46 is provided to determine one or more section of time on the plane of the Doppler frequency f and time t, for eliminating blood backscattering powers P(t) in one or more section of time where the area P corresponding to the blood backscattering is superimposed on the area Q corresponding to the clutter components, when calculating an average of the values of the blood backscattering power. The averaging section setting unit 46 has a construction which is similar to the aforementioned Doppler frequency range setting unit 26 in FIG. 6. During the determination of the elimination section of time, the content of the data buffer memory 20 is not renewed, and the display of the Doppler spectrum on a screen of the display unit 27' is frozen. The elimination section of time is manually input to the averaging section setting unit 46 by the pointing device 46-1. In the averaging section setting unit 46, the operator inputs a start time $t_{start}$, and a stop time $t_{stop}$ for the operation of averaging values of the blood backscattering power. For example, in the example of FIG. 15, the operator can input the times $t_b$ and $t_d$ respectively as start times $t_{start}$, and input the times $t_c$ and $t_e$ respectively as stop times $t_{stop}$, based on a display on the display unit 27' as shown FIG. 15. The pointing device 46-1 may be, for example, a mouse, a track ball, or the like. The input from the pointing device 46-1 is digitized to obtain coordinates of a mouse cursor. The coordinates of a mouse cursor are supplied to the display unit 27' to superimpose a line indicating the start times and the stop times which are input as above, on the Doppler spectrum on a screen of the display as indicated in FIG. 15. In the example of FIG. 15, boundaries of the above area are indicated by dashed lines. These lines can be indicated, for example, by clicking the mouse on a time coordinate corresponding to each of the start times $t_{start}$ and the stop times $t_{stop}$.

In addition, the time coordinates of the start times $t_{start}$ and the stop times $t_{stop}$ are respectively memorized in the start time memory 46-4 and the stop time memory 46-5 in the order in which they occur. The switch 46-3 connects the digitizing unit 46-2 to either of the start time m 46-4 or the stop time memory 46-5, according to whether the start times $t_{start}$ or the stop times $t_{stop}$ are being input. This switch 46-3 may be realized by a manual switch, or by a program wherein the operation is switched from one to another of the inputs of the start times $t_{start}$ and the stop times $t_{stop}$ according to a predetermined command input, for example, a key stroke from a keyboard. Thus, the above start times $t_{start}$ and the stop times $t_{stop}$ are memorized in the corresponding memories 46-4 and 46-5, respectively.

After the above inputs of the start times $t_{start}$ and the stop times $t_{stop}$ are completed, the blood backscattering powers P(t) wherein the data in the aforementioned area Q due to the clutter components have already been eliminated in the blood backscattering power obtaining unit 50, is supplied to the averaging unit 37 to average the blood backscattering powers P(t) to obtain an average $P_{avr}$ of the blood backscattering powers P(t) in the sections which are determine, i.e., selected, by the above start times $t_{start}$ and the stop times $t_{stop}$.

Figure 17:
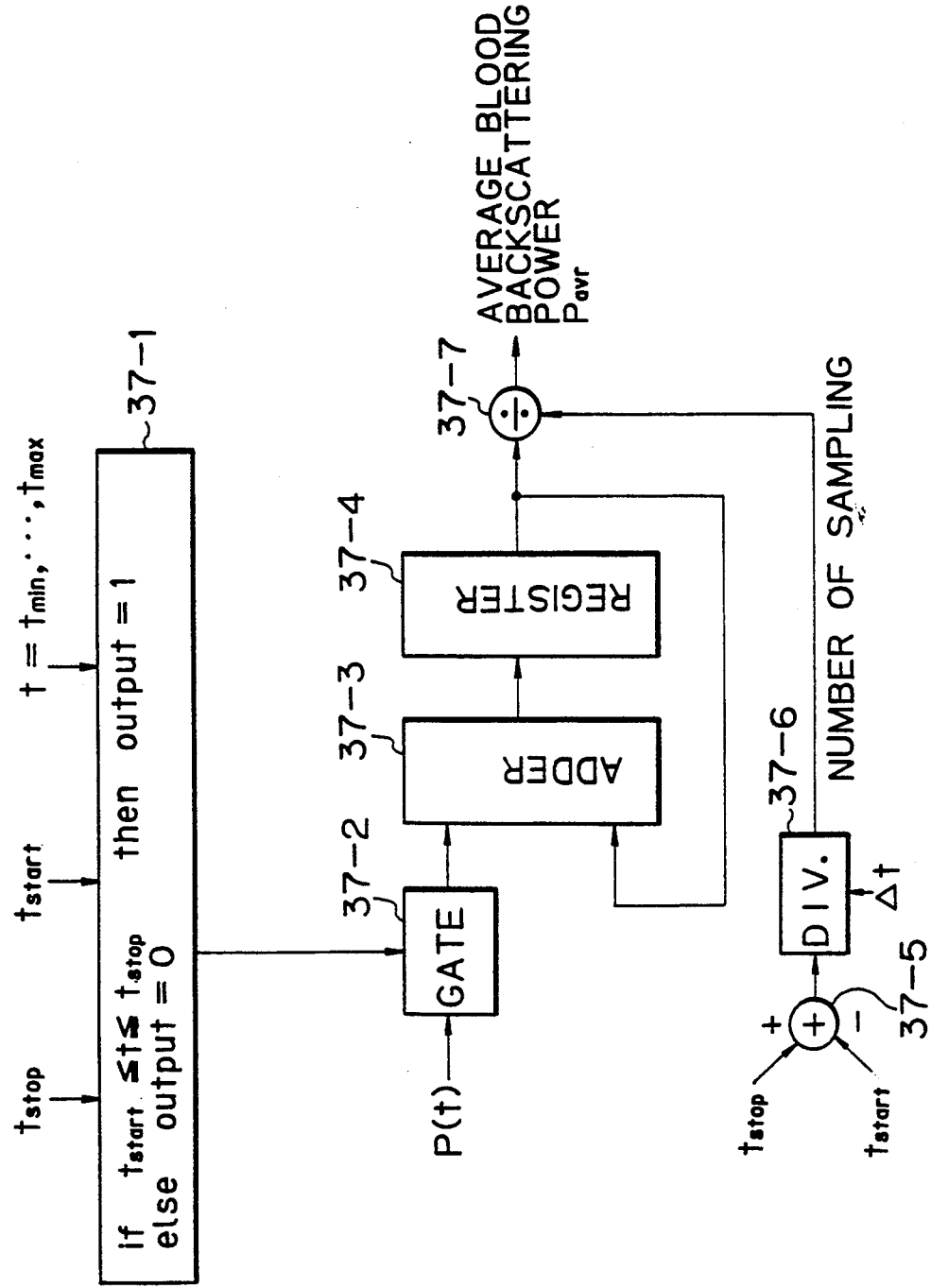
FIG. 17 is a diagram showing an example of a construction of the averaging unit 37 in the construction of FIG. 15.

FIG. 17 is a diagram showing an example construction of the averaging unit 37 in the construction of FIG. 16. In FIG. 17, reference numeral 37-1 denotes a gate control unit, 37-2 denotes a gate, 37-3 denotes an adder, 37-4 denotes a register, 37-5 denotes a subtracter, and 37-6 and 37-7 each denote a divider. The gate control unit 37-1 reads one of the above data of the start times $t_{start}$ in the order of a lapse of tim, i.e., chronological order from the start time memory 46-4, and one of the above data of the stop $t_{stop}$ in the order of a lapse of time from the stop time memory 46-5. Next, the gate control unit 37-1 outputs an active gate control signal to the gate 37-2 to make the gate 37-2 open when the time t of the blood backscattering power P(t) which is currently input into the gate 37-2, satisfies a condition, $t_{start} \leq t \leq t_{stop}$, and outputs an inactive gate control signal to make the gate 37-2 close when the time t of the blood backscattering power P(t) which is currently input into the gate 37-2, does not satisfy the above condition.

Thus, only the blood backscattering power P(t) at the sampling time t which satisfies the condition, $t_{start} \leq t \leq t_{stop}$, is supplied to one of two input terminals of the adder 37-3. The adder 37-3 obtains a sum of two inputs, and the output of the adder 37-3 is applied to the register 37-4. The output of the register 37-4 is applied to the other of the two input terminals of the adder 37-3. Thus, the blood backscattering power P(t) at the sampling time t which satisfies the condition, $t_{start} \leq t \leq t_{stop}$, is accumulated in the register 37-4.

Parallel to the accumulation, one of the above start times $t_{start}$ and the corresponding one of the stop times $t_{stop}$ are input into the subtracter 37-5 to obtain a duration $t_{start}-t_{stop}$ of the above accumulation. The duration $t_{start}-t_{stop}$ is divided by the sampling cycle At in the divider 37-6 to obtain the number of the accumulations which are carried out in the adder 37-3. Then, the above accumulated value, i.e., the output of the register 37-4, is divided by the above number of the accumulations for the above duration $t_{start}-t_{stop}$, to obtain the averaged blood backscattering power $P_{avr}$. Namely, the averaged blood backscattering power $P_{avr}$ is expressed as $$P_{avr} = \frac{\Delta t}{t_{stop} - t_{start}} \left( \sum_{t=t_{start}}^{t_{stop}} P(t) \right).$$

Thereafter, the above operation is repeated for the next one of the above sections which have been determined in the averaging section setting unit 46.

SIXTH EMBODIMENT (FIGS. 18, 19, AND 20)

Figure 18:
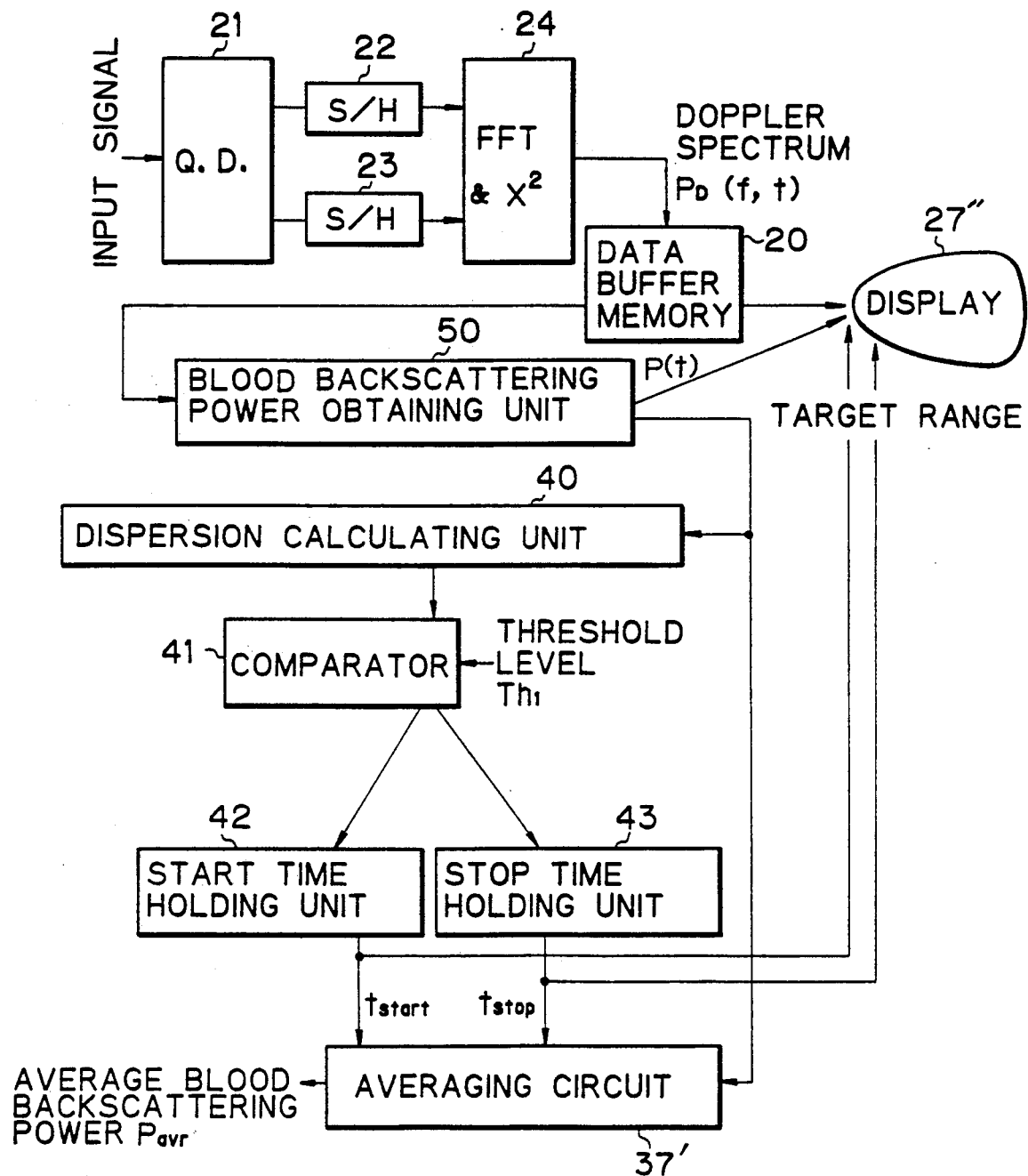
FIG. 18 is a diagram showing a construction of a sixth embodiment of the present invention.

FIG. 18 is a diagram showing a construction of a sixth embodiment of the present invention. In FIG. 18, reference numeral 27" denotes a display control circuit, 40 denotes a dispersion calculating unit, 41 denotes a comparator, 42 denotes a start time holding unit, and 43 denotes a stop time holding unit. In FIG. 18, the data buffer memory 20, the quadrature detector unit 21, the sample & hold circuits 22 and 23, and the Doppler spectrum calculating unit 24, the constructions of the accumulating unit 25, which is part of element 50 the averaging circuit 37', i.e., averaging unit, and the blood backscattering power obtaining unit 50, are respectively similar to the corresponding constructions of FIG. 16. In addition, the display unit 27" represents the display unit 27 and the display control unit 32 or 32' in the constructions of FIGS. 9, 11, and 13, except that the display unit 27" further functions as explained below.

Figure 19:
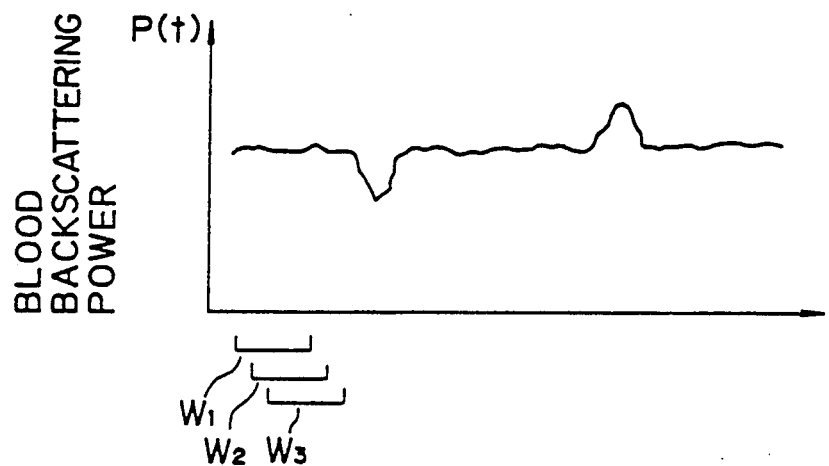
FIG. 19 is a diagram showing an example of a fluctuation of the blood backscattering power.

FIG. 19 is a diagram showing an example of the fluctuation of the blood backscattering power P(t) which is obtained in the constructions of FIGS. 6, 9, 11, and 13. As shown in FIG. 19, the curve of the blood backscattering power P(t) shows a valley and a peak, and it is considered that the credibility of the data of the blood backscattering power P(t) is low in the sections of time wherein the above valley and peak appear. Therefore, the data of the blood backscattering power P(t), in the sections of time wherein the above valley and peak appear, should be eliminated when calculating the average of the blood backscattering power. According to the sixth embodiment of the present invention, the average of the blood backscattering power is automatically calculated, eliminating the data of the blood backscattering power P(t) in the sections of time wherein the above valley and peak appear, without freezing data or manually setting the sections for the elimination, as explained below.

The dispersion calculating unit 40 in FIG. 18 generates a plurality of windows $W_1$, $W_2$, $W_3$, ... as indicated in FIG. 19, and calculates and outputs dispersions $\sigma$ of the data of the blood backscattering power P(t) in the respective windows. The output of the dispersion calculating unit 40 is supplied to the comparator 41. The dispersion $\sigma$ is defined as $$\sigma = \frac{1}{N} \Sigma (P(t) - \overline{P(t)})^2,$$

where N is a number of sampling in the window, and $$\overline{P(t)} = \frac{1}{N} \Sigma P(t).$$

Figure 20A:
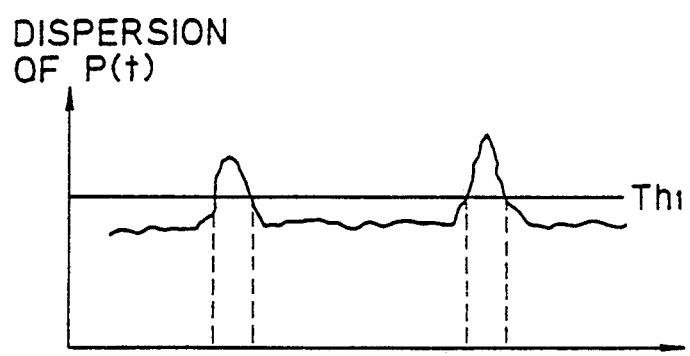
FIGS. 20A and 20B are diagrams showing an example of an operation of the comparator 41 in FIG. 18.
Figure 20B:
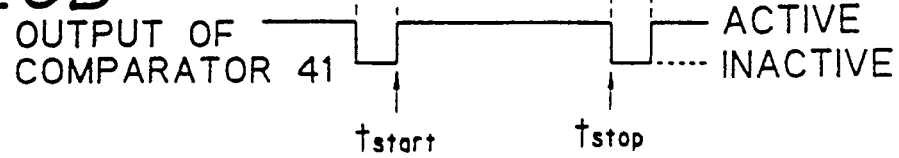

The comparator 41 compares the supplied dispersion with a threshold value $Th_1$, to output an active signal, to the start time holding unit 42 and the stop time holding unit 43, when the dispersion is less than the threshold value $Th_1$, and to output inactive signal, to the start time holding unit 42 and the stop time holding unit 43, when the dispersion is not less than the threshold value $Th_1$, as shown in FIGS. 20A and 20B. FIGS. 20A and 20B are diagrams showing an example of the operation of the comparator 41 in FIG. 18. The threshold value $Th_1$ is determined, for example, by experiment so that the above-mentioned valley and peak in the curve of the blood backscattering power P(t) are eliminated, and is preset to the comparator 41.

When the above output of the comparator 41 transits from the inactive level to the active level, as indicated by $t_2$ in FIG. 20B, the start time holding unit 42 memorizes the time at which the transition occurs, as a start time $t_{start}$. When the above output of the comparator 41 transits from the active level to the inactive level as indicated by $t_3$ in FIG. 20B, after the above transition from the inactive level to the active level, the stop time holding unit 43 memorizes the time at which the transition from the active level to the inactive level occurs, as a stop time $t_{stop}$ corresponding to the start time $t_{start}$ which is last memorized. The memorized start time $t_{start}$ and stop time $t_{stop}$ are supplied to the averaging unit 37'. Further start times $t_{start}$ and corresponding stop times $t_{stop}$ are respectively stored in the start time holding unit 42 and the stop time holding unit 43 in the order of the lapse of time, in response to occurrences of the transitions as above.

The averaging unit 37' in FIG. 18 operates basically in the same way as that in FIG. 16, except that the averaging unit 37' in FIG. 18 can constantly operate because the construction of FIG. 18 is not frozen for setting the sections of time for eliminating data of the blood backscattering power, and that the start time $t_{start}$ and stop time $t_{stop}$ are supplied from the start time holding unit 42 and the stop time holding unit 43. Thus, the averaged blood backscattering power $P_{avr}$ is expressed as $$P_{avr} = \frac{\Delta t}{t_{stop} - t_{start}} \left( \sum_{t=t_{start}}^{t_{stop}} P(t) \right).$$

The above start time $t_{start}$ and stop time $t_{stop}$ are also supplied from the start time holding unit 42 and the stop time holding unit 43 to the display unit 27". Receiving these times, the display unit 27" indicates the above start time $t_{start}$ and stop time $t_{stop}$ on the screen, for example, as shown in FIG. 15.

I claim:

1. An apparatus for obtaining a blood backscattering power, comprising:
   ultrasound signal transmitting means for transmitting an ultrasound signal into various portions of a human body at certain depths, said various portions including bodily tissues and blood within blood vessels;
   signal converting means for receiving an ultrasound signal which is generated in said various portions in the human body by reflecting or backscattering the transmitted ultrasound signal, and converting the received ultrasound signal to an electric signal;
   signal input means for inputting said electric signal;
   Doppler spectrum obtaining means for obtaining a Doppler spectrum which contains information on the distribution of the intensity of said electric signal as a function of time and a Doppler frequency, where the Doppler frequency is a quantity indicating a velocity component in a direction of said transmitted ultrasound signal, of said various portions which backscatter or reflect said transmitted ultrasound signal;
   Doppler frequency range determining means for determining a variable elimination frequency range of said Doppler frequency for each of a plurality of determination times; and
   accumulating means for accumulating said intensity over a whole range of said Doppler frequency except said elimination frequency range for each determination time, to obtain a blood backscattering power as a function of time.

2. An apparatus according to claim 1, wherein said Doppler frequency range determining means comprises input means for manually inputting said elimination frequency range for each determination time.

3. An apparatus according to claim 2, wherein said Doppler frequency range determining means comprises memory means for memorizing said elimination frequency range for each determination time.

4. An apparatus according to claim 2, wherein said Doppler frequency range determining means comprises display means for displaying said Doppler spectrum, and said elimination frequency range so that the elimination frequency range can be determined based on the shape of the Doppler spectrum.

5. An apparatus according to claim 1, wherein said Doppler frequency range determining means comprises comparator means for comparing said intensity with a threshold level.

6. An apparatus according to claim 5, wherein said accumulating means comprises gate means for receiving the output of said comparator means and not allowing a supply of said intensity to pass to the accumulating means when said intensity is larger than said threshold level.

7. An apparatus according to claim 5, wherein said Doppler frequency range determining means further comprises elimination range modifying means for widening said elimination frequency range so that the electric signal in the Doppler frequencies in the vicinity of the pre-widened elimination frequency range on both sides thereof, is excluded from the operation in said accumulating means.

8. An apparatus according to claim 1, further comprising:
   time range determining means for determining an effective time range of the time; and
   averaging means for averaging said blood backscattering power over said effective time range of the time, to obtain an average of said blood backscattering power in said effective time range.

9. An apparatus according to claim 8, wherein said time range determining means comprises input means for manually inputting said effective time range.

10. An apparatus according to claim 9, wherein said time range determining means comprises memory means for memorizing said effective time range.

11. An apparatus according to claim 9, wherein said time range determining means comprises display means for displaying said Doppler spectrum, and said effective time range.

12. An apparatus for obtaining a blood backscattering power, comprising:
    ultrasound transmitting means for transmitting an ultrasound signal into various portions of a human body at certain depths, said various portions including bodily tissues and blood within blood vessels;
    signal converting means for receiving an ultrasound signal which is generated in said various portions in the human body by reflecting or backscattering the transmitted ultrasound signal, and converting the received ultrasound signal to an electric signal;
    signal input means for inputting said electric signal;
    Doppler spectrum obtaining means for obtaining a Doppler spectrum which contains information on the distribution of the intensity of said electric signal as a function of time and a Doppler frequency, where the Doppler frequency is a quantity indicating a velocity component in a direction of said transmitted ultrasound signal, of said various portions which backscatter or reflect said transmitted ultrasound signal;
    Doppler frequency range determining means for determining a variable elimination frequency range of said Doppler frequency for each of a plurality of determination times, said Doppler frequency range determining means comprising:
      comparator means for comparing said intensity with a threshold level; and
      boundaries determining means for determining a beginning point of said elimination frequency range as a Doppler frequency at which said intensity first becomes larger than said threshold level when scanning a whole range of the Doppler frequency for each time, and determining an end point of said elimination frequency range as a Doppler frequency at which said intensity last becomes smaller than said threshold level when scanning a whole range of the Doppler frequency of each determination time; and
    accumulating means for accumulating said intensity over a whole range of said Doppler frequency except said elimination frequency range for each determination time, to obtain a blood backscattering power as a function of time.

13. An apparatus according to claim 12, wherein said accumulating means comprises a gate means for receiving said beginning point and said end point to begin to stop a supply of said intensity to the accumulating means at said beginning point, and start the supply of said intensity to the accumulating means at said end point 14. An apparatus according to claim 13, wherein said Doppler frequency range determining means further comprises boundaries shifting means for shifting said beginning point of said elimination frequency range by a predetermined amount and shifting said end point of said elimination frequency range by a predetermined amount so that said elimination frequency range is widened to exclude the electric signal in the Doppler frequencies in the vicinity of the pre-widened elimination frequency range, on both sides thereof, from the accumulating operation in said accumulating means.

15. An apparatus for obtaining a blood backscattering power, comprising:
  ultrasound signal transmitting means for transmitting an ultrasound signal into various portions of a human body at a certain depths, said various portions including bodily tissues and blood within blood vessels;
  signal converting means for receiving an ultrasound signal which is generated in said various portions in the human body by reflecting or backscattering the transmitted ultrasound signal, and converting the received ultrasound signal to an electric signal;
  signal input means for inputting said electric signal;
  Doppler spectrum obtaining means for obtaining a Doppler spectrum which contains information on the distribution of the intensity of said electric signal as a function of time and a Doppler frequency, where the Doppler frequency is a quantity indicating a velocity component in a direction of a said transmitted ultrasound signal, of said various portions which backscatter or reflect said transmitted ultrasound signal;
  Doppler frequency range determining means for determining a variable elimination frequency range of said Doppler frequency for each of a plurality of determination times;
  accumulating means for accumulating said intensity over a whole range of said Doppler frequency except said elimination frequency range for each determination time, to obtain a blood backscattering power as a function of time;
  time range determining means for determining an effective range of the time, said time range determining means comprising:
    dispersion obtaining means for obtain a dispersion of said blood backscattering power, as a function of said time; and
    comparator means for comparing said dispersion with a threshold level; and
  averaging means for averaging said blood backscattering power over said effective time range of the time, to obtain an average of said blood backscattering power in said effective time range.

16. An apparatus according to claim 15, wherein said averaging means comprises gate means for receiving the output of said comparator means and not allowing a supply of said blood backscattering power to pass to the averaging means when said dispersion is larger than said threshold level.

17. An apparatus according to claim 15, wherein said time range determining means comprises boundaries determining means for determining a beginning point of said effective time range as a time at which said dispersion becomes smaller than said threshold level, and determining an end point of said effective time range as a time at which said dispersion becomes larger than said threshold level.

18. An apparatus according to claim 17, wherein said averaging means comprises gate means for receiving said beginning point and said end point to stop a supply of said blood backscattering power to the averaging means at said beginning point, and start supply of said blood backscattering power to the averaging means at said end point.

* * * * *

UNITED STATES PATENT AND TRADEMARK OFFICE
CERTIFICATE OF CORRECTION

PATENT NO. : 5,243,987
DATED : Sep. 14, 1993
INVENTOR(S) : SHIBA

It is certified that error appears in the above-indentified patent and that said Letters Patent is hereby corrected as shown below:

TITLE PAGE:

[56] References Cited, after the first document listed under FOREIGN PATENT DOCUMENTS, insert the following:

--0383288   8/1990   European Pat. Off.--

Under OTHER PUBLICATIONS, delete the first reference "Yamada, I. et al ... 1990."

[57] ABSTRACT, line 23, change "efective" to --effective--.

Col. 1,   line 52, after "transducer" insert --,--.

Col. 2,   line 16, change "the a" to --the--;
line 17, after "notes" insert --a--;
line 61, change "while" to --which--.

Col. 3,   line 11, after "object" insert --,--;
line 16, after "times" insert --;--; and after "for" insert --accumulating the--;
line 63, after "scanning" insert --a--.

Col. 4,   line 55, change "t the" to --to the--.

Col. 5,   line 29, change "clutters" to --clutter--.

UNITED STATES PATENT AND TRADEMARK OFFICE
CERTIFICATE OF CORRECTION

PATENT NO. : 5,243,987
DATED : Sep. 14, 1993
INVENTOR(S) : SHIBA

It is certified that error appears in the above-indentified patent and that said Letters Patent is hereby corrected as shown below:

Col. 6, line 31, change "numeral" to --numerals--.

Col. 7, line 12, change "si$\omega$t" to --sin$\omega$t--.

Col. 9, line 38, delete "Fourier";
line 55, change "27, shown" to --27 shown,--.

Col. 10, line 18, after "trace of the" insert --cursor of a pointing device, e.g., mouse--;
line 19, delete "i.e., a plot of frequency versus time".

Col. 11, line 4, change "PD(f,t)" to --$P_D(f,t)$--;
line 6, change "PD(f,t)" to --$P_D(f,t)$--;
line 13, change "$P_D$f,t)" to --$P_D(f,t)$--;
line 56, change "The" to --Th$_o$--.

Col. 12, line 20, in the equation, change "$P_d(f,t)<Th_o$" to --$P_D(f,t)<Th_o$--.

Col. 13, line 24, change "PD(f,t)" to --$P_D(f,t)$--.

Col. 14, line 2, delete "the" (second occurrence).

Col. 15, line 14, change "hot" to --not--;
line 27, after "ponents" insert --.--;
line 56, change "section" to --sections--.

UNITED STATES PATENT AND TRADEMARK OFFICE
CERTIFICATE OF CORRECTION

PATENT NO. : 5,243,987
DATED : Sep. 14, 1993
INVENTOR(S) : SHIBA

It is certified that error appears in the above-indentified patent and that said Letters Patent is hereby corrected as shown below:

Col. 16, line 5, change "$t_{starts,}$" to --$t_{start}$--;
 line 10, after "shown" insert --in--;
 line 28, change "time m" to --time memory--;
 line 56, change "tim," to --time,--;
 line 58, after "stop" insert --time--.

Col. 18, line 22, after "output" insert --an--.

Col. 21, line 18 (claim 15, line 5), delete "a";
 line 32 (claim 15, line 19), delete "a" (third occurrence).

Col. 22, line 36 (claim 18, line 5), after "start" insert --the--.

Signed and Sealed this

Twenty-seventh Day of May, 1997

Attest:

BRUCE LEHMAN

Attesting Officer

Commissioner of Patents and Trademarks